United States Patent
Pic et al.

(10) Patent No.: US 11,766,546 B2
(45) Date of Patent: Sep. 26, 2023

(54) APPARATUSES AND METHODS FOR DELIVERING POWDERED AGENTS

(71) Applicant: Boston Scientific Scimed, Inc., Maple Grove, MN (US)

(72) Inventors: Andrew Pic, Northboro, MA (US); Matthew Laplaca, Franklin, MA (US); Jeffrey V. Bean, Fitchburg, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1278 days.

(21) Appl. No.: 16/259,024

(22) Filed: Jan. 28, 2019

(65) Prior Publication Data

US 2019/0232030 A1     Aug. 1, 2019

Related U.S. Application Data

(60) Provisional application No. 62/624,417, filed on Jan. 31, 2018.

(51) Int. Cl.
*A61M 31/00*     (2006.01)
*A61M 25/00*     (2006.01)
(Continued)

(52) U.S. Cl.
CPC ....... *A61M 31/00* (2013.01); *A61B 17/12181* (2013.01); *A61M 13/00* (2013.01);
(Continued)

(58) Field of Classification Search
CPC .. A61M 31/00; A61M 13/00; A61M 25/0043; A61M 2202/064; A61M 5/3015; A61B 17/12181; A61L 2400/04
See application file for complete search history.

(56) References Cited

U.S. PATENT DOCUMENTS 471,854 A     3/1892   Howard
881,238 A     3/1908   Hasbrouck
(Continued)

FOREIGN PATENT DOCUMENTS

CN     101401956 B     11/2012
DE     60215438 T2     8/2007
(Continued)

OTHER PUBLICATIONS

Bridevaux, Pierre-Olivier, et al. "Short-term safety of thoracoscopic talc pleurodesis for recurrent primary spontaneous pneumothorax: a prospective European multicentre study." European Respiratory Journal 38.4 (2011): 770-773.
(Continued)

*Primary Examiner* — Lauren P Farrar
(74) *Attorney, Agent, or Firm* — Bookoff McAndrews, PLLC

(57) ABSTRACT

An apparatus for delivering a powdered agent into a subject's body may include a first passage for receiving a pressurized gas. The apparatus also may include a container housing a powdered agent. The container may be in fluid connection with the first passage. At least a portion of the pressurized gas is introduced into the powdered agent in the container to fluidize the powdered agent. The apparatus also may include a second passage for receiving the powdered agent from the container. In a first configuration of the apparatus, the second passage may not be in fluid connection with the container. In a second configuration of the apparatus, the second passage may be in fluid connection with the container. The apparatus may be configured to transition between the first configuration and the second configuration.

20 Claims, 11 Drawing Sheets

(51) Int. Cl.
*A61B 17/12* (2006.01)
*A61M 13/00* (2006.01)

(52) U.S. Cl.
CPC ...... *A61M 25/0043* (2013.01); *A61L 2400/04* (2013.01); *A61M 2202/064* (2013.01)

(56) References Cited

U.S. PATENT DOCUMENTS

| | | | |
|---|---|---|---|
| 1,145,520 A | 7/1915 | Smith | |
| 1,599,959 A | 9/1926 | Buheiji | |
| 1,732,566 A | 10/1929 | McKendrick | |
| 2,151,418 A | 3/1939 | Bolté | |
| 2,185,927 A | 6/1940 | Shelanski | |
| 2,478,715 A | 8/1949 | Schmitt | |
| 2,623,519 A | 12/1952 | Cohen | |
| 3,669,113 A | 6/1972 | Altounyan et al. | |
| 3,940,061 A | 2/1976 | Gimple et al. | |
| 4,184,258 A | 6/1980 | Barrington et al. | |
| 4,427,450 A | 1/1984 | Kostansek | |
| 4,457,329 A | 7/1984 | Werley et al. | |
| 4,806,167 A | 2/1989 | Raythatha | |
| 5,215,221 A | 6/1993 | Dirksing | |
| 5,231,983 A | 8/1993 | Matson et al. | |
| 5,273,531 A | 12/1993 | Knoepfler | |
| 5,312,331 A | 5/1994 | Kneopfler | |
| 5,312,333 A | 5/1994 | Churinetz et al. | |
| 5,366,122 A | 11/1994 | Guentert et al. | |
| 5,445,612 A | 8/1995 | Ferakura et al. | |
| 5,470,311 A | 11/1995 | Setterstrom et al. | |
| 5,884,621 A | 3/1999 | Matsugi et al. | |
| 5,951,531 A | 9/1999 | Ferdman et al. | |
| 5,989,215 A | 11/1999 | Delmotte et al. | |
| 6,003,512 A | 12/1999 | Gerde | |
| 6,484,750 B1 | 11/2002 | Foos et al. | |
| 6,554,022 B2 | 4/2003 | Wakeman | |
| 6,589,087 B2 | 7/2003 | Mackal et al. | |
| 6,684,917 B2 | 2/2004 | Zhu et al. | |
| 6,708,712 B2 | 3/2004 | Wakeman | |
| 6,716,190 B1 | 4/2004 | Glines et al. | |
| 6,799,571 B1 | 10/2004 | Hughes et al. | |
| 7,178,547 B2 | 2/2007 | Mackal | |
| 7,311,270 B2 | 12/2007 | Kapila | |
| 7,334,598 B1 | 2/2008 | Hollars | |
| 7,361,300 B2 | 4/2008 | Kelly et al. | |
| 7,427,607 B2 | 9/2008 | Suzuki | |
| 7,455,248 B2 | 11/2008 | Kablik et al. | |
| 7,461,649 B2 | 12/2008 | Gamard et al. | |
| 7,544,177 B2 | 6/2009 | Gertner | |
| 7,563,299 B2 | 7/2009 | Baptista da Costa et al. | |
| 7,673,647 B2 | 3/2010 | Mackal | |
| 7,841,338 B2 | 11/2010 | Dunne et al. | |
| 7,892,205 B2 | 2/2011 | Palasis et al. | |
| 7,921,874 B2 | 4/2011 | Tekulve et al. | |
| 8,037,880 B2 | 10/2011 | Zhu et al. | |
| 8,097,071 B2 | 1/2012 | Burgess et al. | |
| 8,118,777 B2 | 2/2012 | Ducharme et al. | |
| 8,269,058 B2 | 9/2012 | McCarthy et al. | |
| 8,313,474 B2 | 11/2012 | Campbell et al. | |
| 8,360,276 B2 | 1/2013 | Rogier et al. | |
| 8,361,054 B2 | 1/2013 | Ducharme et al. | |
| 8,496,189 B2 | 7/2013 | Lomond et al. | |
| 20,130,218 | 8/2013 | Kubo | |
| 8,673,065 B2 | 3/2014 | Burgess et al. | |
| 8,721,582 B2 | 5/2014 | Ji | |
| 8,728,032 B2 | 5/2014 | Ducharme et al. | |
| 8,741,335 B2 | 6/2014 | McCarthy | |
| 8,827,980 B2 | 9/2014 | Ji | |
| 8,910,627 B2 | 12/2014 | Iwatschenko et al. | |
| 8,951,565 B2 | 2/2015 | McCarthy | |
| 9,028,437 B2 | 5/2015 | Ott et al. | |
| 9,089,658 B2 | 7/2015 | Dunne et al. | |
| 9,101,744 B2 | 8/2015 | Ducharme | |
| 9,107,668 B2 | 8/2015 | Melsheimer et al. | |
| 9,132,206 B2 | 9/2015 | McCarthy | |
| 9,204,957 B2 | 12/2015 | Gregory et al. | |
| 9,205,170 B2 | 12/2015 | Lucchesi et al. | |
| 9,205,207 B2 | 12/2015 | Ji | |
| 9,205,240 B2* | 12/2015 | Greenhalgh | A61M 15/0008 |
| 9,308,584 B2 | 4/2016 | Burgess et al. | |
| 9,310,812 B2 | 4/2016 | Costle et al. | |
| 9,375,533 B2 | 6/2016 | Ducharme et al. | |
| 9,492,646 B2 | 11/2016 | Hoogenakker et al. | |
| 9,517,976 B2 | 12/2016 | Mackal | |
| 9,545,490 B2 | 1/2017 | Iwatschenko et al. | |
| 9,555,185 B2 | 1/2017 | Foster et al. | |
| 9,629,966 B2 | 4/2017 | Ji | |
| 9,636,470 B2 | 5/2017 | Pohlmann et al. | |
| 9,707,359 B2 | 7/2017 | Kubo | |
| 9,713,682 B2 | 7/2017 | Eistetter et al. | |
| 9,717,897 B2 | 8/2017 | Rogier | |
| 9,821,084 B2 | 11/2017 | Diegelmann et al. | |
| 9,839,772 B2 | 12/2017 | Ducharme | |
| 9,839,774 B2 | 12/2017 | Bonaldo | |
| 9,846,439 B2 | 12/2017 | Carman et al. | |
| 9,867,931 B2 | 1/2018 | Gittard | |
| 9,976,660 B2 | 5/2018 | Stanton et al. | |
| 10,004,690 B2 | 6/2018 | Lee et al. | |
| 10,010,705 B2 | 7/2018 | Greenhalgh et al. | |
| 10,017,231 B2 | 7/2018 | Fawcett, Jr. | |
| 10,036,617 B2 | 7/2018 | Mackal | |
| 10,065,004 B2 | 9/2018 | Eder et al. | |
| 10,173,019 B2 | 1/2019 | Kaufmann et al. | |
| 10,384,049 B2 | 8/2019 | Stanton et al. | |
| 10,463,811 B2 | 11/2019 | Lee et al. | |
| 10,507,293 B2 | 12/2019 | Goodman et al. | |
| 10,646,706 B2 | 5/2020 | Rogier | |
| 10,730,595 B2 | 8/2020 | Fawcett | |
| 10,751,523 B2 | 8/2020 | Rogier | |
| 10,806,853 B2 | 10/2020 | Gittard | |
| 10,850,814 B2 | 12/2020 | Fawcett | |
| 10,994,818 B2 | 5/2021 | Hernandez | |
| 2004/0107963 A1 | 6/2004 | Finlay et al. | |
| 2004/0249359 A1 | 12/2004 | Palasis et al. | |
| 2005/0121025 A1 | 6/2005 | Gamard et al. | |
| 2005/0147656 A1 | 7/2005 | McCarthy et al. | |
| 2005/0220721 A1 | 10/2005 | Kablik et al. | |
| 2006/0004314 A1 | 1/2006 | McCarthy et al. | |
| 2006/0213514 A1 | 9/2006 | Price et al. | |
| 2007/0056586 A1 | 3/2007 | Price et al. | |
| 2007/0066920 A1 | 3/2007 | Hopman et al. | |
| 2007/0066924 A1 | 3/2007 | Hopman et al. | |
| 2007/0082023 A1 | 4/2007 | Hopman et al. | |
| 2007/0125375 A1 | 6/2007 | Finlay et al. | |
| 2007/0151560 A1 | 7/2007 | Price et al. | |
| 2007/0083137 A1 | 8/2007 | Hopman et al. | |
| 2007/0199824 A1 | 8/2007 | Hoerr et al. | |
| 2008/0021374 A1 | 1/2008 | Kawata | |
| 2008/0287907 A1 | 11/2008 | Gregory et al. | |
| 2009/0101144 A1 | 4/2009 | Gamard et al. | |
| 2009/0155342 A1 | 6/2009 | Diegemann et al. | |
| 2009/0281486 A1 | 11/2009 | Ducharme | |
| 2010/0121261 A1 | 5/2010 | Kablik et al. | |
| 2010/0305505 A1* | 12/2010 | Ducharme | A61M 11/02 604/118 |
| 2011/0073200 A1 | 3/2011 | Overvaag et al. | |
| 2011/0274726 A1 | 11/2011 | Guo et al. | |
| 2011/0308516 A1 | 12/2011 | Price et al. | |
| 2013/0218072 A1* | 8/2013 | Kubo | A61M 13/00 604/58 |
| 2014/0271491 A1 | 9/2014 | Gittard et al. | |
| 2015/0094649 A1 | 4/2015 | Gittard | |
| 2015/0125513 A1 | 5/2015 | McCarthy | |
| 2016/0375202 A1 | 12/2016 | Goodman et al. | |
| 2017/0106181 A1 | 4/2017 | Bonaldo et al. | |
| 2017/0119980 A1* | 5/2017 | Eder | A61M 13/00 |
| 2017/0232141 A1 | 8/2017 | Surti et al. | |
| 2017/0252479 A1 | 9/2017 | Ji et al. | |
| 2017/0296760 A1 | 10/2017 | Lee et al. | |
| 2018/0099088 A1 | 4/2018 | Gittard | |
| 2018/0193574 A1 | 7/2018 | Smith et al. | |
| 2018/0214160 A1 | 8/2018 | Hoskins et al. | |
| 2018/0339144 A1 | 11/2018 | Greenhalgh et al. | |
| 2019/0134366 A1 | 5/2019 | Erez et al. | |
| 2019/0217315 A1 | 7/2019 | Maguire et al. | |

(56) References Cited

U.S. PATENT DOCUMENTS

| | | |
|---|---|---|
| 2019/0232030 A1 | 8/2019 | Pic et al. |
| 2021/0024187 A1 | 1/2021 | Fawcett et al. |
| 2021/0069485 A1 | 3/2021 | Rogier |

FOREIGN PATENT DOCUMENTS

| | | |
|---|---|---|
| EP | 1 821 083 A1 | 8/2007 |
| EP | 3052168 B1 | 11/2019 |
| JP | H07118305 A | 5/1995 |
| WO | 03013552 A1 | 2/2003 |
| WO | 2004066806 A2 | 8/2004 |
| WO | 2005062896 A2 | 7/2005 |
| WO | 2006071649 A2 | 7/2006 |
| WO | 2006088912 A2 | 8/2006 |
| WO | 2008033462 A2 | 3/2008 |
| WO | 2009061409 A1 | 5/2009 |
| WO | 2015050814 A1 | 4/2015 |
| WO | 2018157772 A1 | 9/2018 |

OTHER PUBLICATIONS

Giday, Samuel, et al. "Safety analysis of a hemostatic powder in a porcine model of acute severe gastric bleeding." Digestive diseases and sciences 58.12 (2013): 3422-3428.

Giday, Samuel A., et al. "A long-term randomized controlled trial of a novel nanopowder hemostatic agent for control of severe upper gastrointestinal bleeding in a porcine model." Gastrointestinal Endoscopy 69.5 (2009): AB133.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299.

Regalia, Kristen, et al. "Hemospray in Gastrointestinal Bleeding." Practical Gastroenterology. Endoscopy: Opening New Eyes, ser. 8, May 2014, pp. 13-24. 8.

Cook Medical. Hemospray Endoscopic Hemostat, COOK, 2014. (7 pages, in English).

"Hemospray Clinical Experience Shows Efficacy of a New Hemostasis Modality—v1", Cook Medical, 2012.

"Hemospray Clinical Experience Shows Efficacy of a New Hemostasis Modality—v2", Cook Medical, 2013.

"Hemospray Clinical Experience Shows Efficacy of a New Hemostasis Modality—v3", Cook Medical, 2014.

Aslanian, Harry R., and Loren Laine. "Hemostatic powder spray for GI bleeding." Gastrointestinal endoscopy 77.3 (2013): 508-510.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299. via ResearchGate.

RETSCH GmbH Haan. Sieve Analysis: Taking a Close Look at Quality, An Expert Guide to Particle Size Analysis. 2015. (56 pages, in English).

Micromeritics. Density Analysis, 2001. (6 pages, in English).

Micromeritics. "Application Note: Bulk and Skeletal Density Computations for the AutoPore." May 2012. (3 pages, in English).

Arefnia, Ali, et al. "Comparative Study on the Effect of Tire-Derived Aggregate on Specific Gravity of Kaolin." Electronic Journal of Geotechnical Engineering 18 (2013): 335-44.

Kesavan, Jana, et al. "Density Measurements of Materials Used in Aerosol Studies". Edgewood Chemical Biological Center Aberdeen Proving Ground MD, 2000.

\* cited by examiner

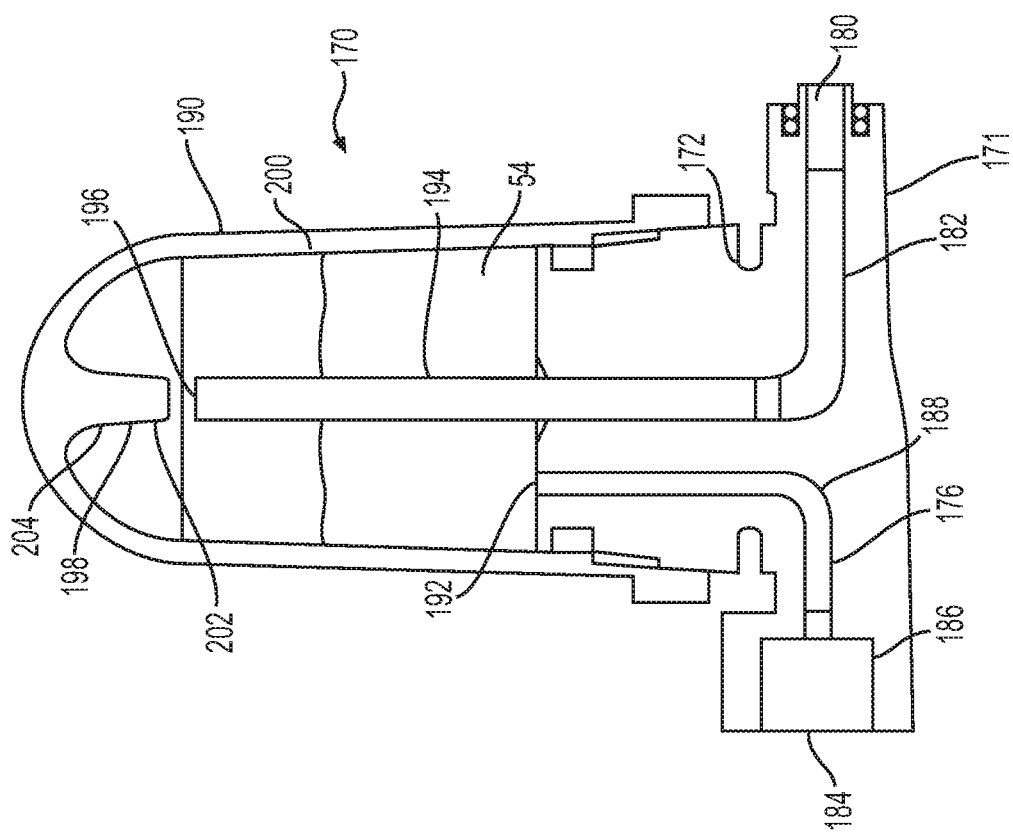
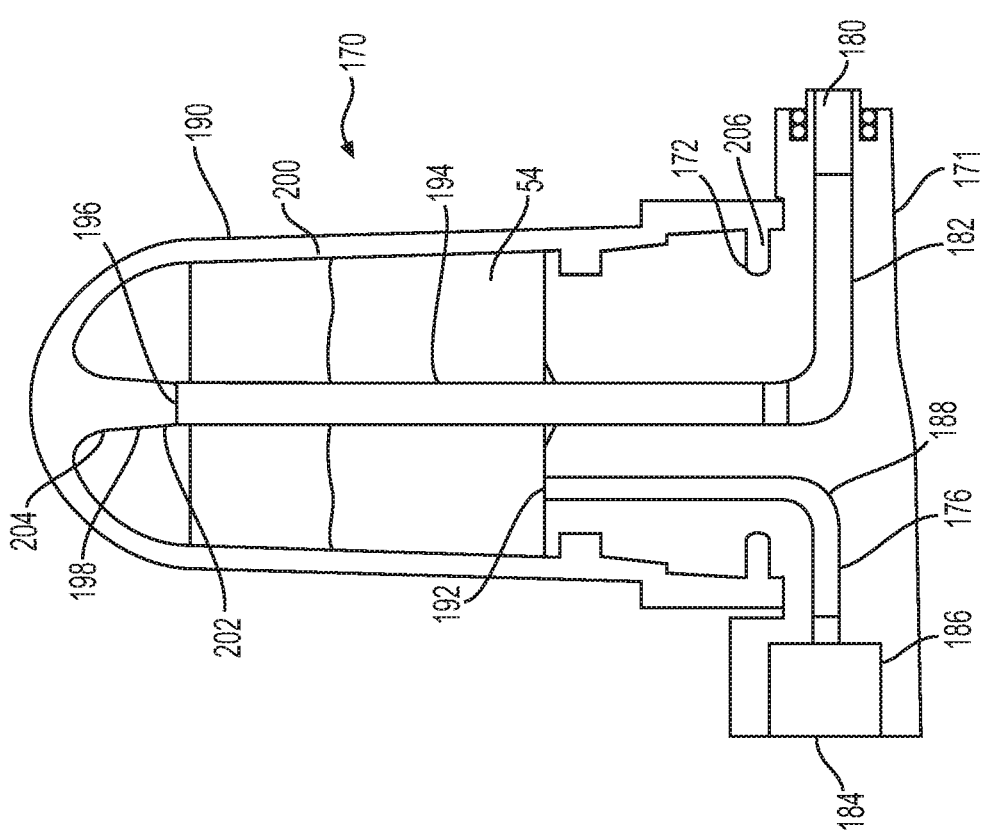

US 11,766,546 B2

APPARATUSES AND METHODS FOR DELIVERING POWDERED AGENTS

CROSS-REFERENCE TO RELATED APPLICATIONS

This application claims the benefit of priority from U.S. Provisional Application No. 62/624,417, filed on Jan. 31, 2018, which is incorporated by reference herein in its entirety.

TECHNICAL FIELD

Various aspects of the present disclosure relate generally to apparatuses and methods for delivering powdered agents. More specifically, the present disclosure relates to apparatuses and methods for the endoscopic delivery of hemostatic powders.

BACKGROUND

When bleeding occurs in a subject's body during a medical procedure, a user performing the procedure may seek ways in which to reduce or to eliminate the bleeding. One way to manage bleeding is by applying a hemostatic powder at a site of the bleeding. Where the medical procedure being performed is an endoscopic procedure, applying the hemostatic powder at the site may entail delivering the powder to the site using a catheter. Ensuring that the hemostatic powder can be properly delivered to the site through the catheter may lead to improved outcomes.

SUMMARY

Aspects of the present disclosure relate to, among other things, apparatuses and methods for delivering powdered agents. Each of the aspects disclosed herein may include one or more of the features described in connection with any of the other disclosed aspects.

In one example, an apparatus for delivering a powdered agent into a subject's body may include a first passage for receiving a pressurized gas. The apparatus also may include a container housing a powdered agent. The container may be in fluid connection with the first passage. At least a portion of the pressurized gas may be introduced into the powdered agent in the container to fluidize the powdered agent. The apparatus also may include a second passage for receiving the powdered agent from the container. In a first configuration of the apparatus, the second passage may not be in fluid connection with the container. In a second configuration of the apparatus, the second passage may be in fluid connection with the container. The apparatus may be configured to transition between the first configuration and the second configuration.

Any example of the apparatuses for delivering a powdered agent into a subject's body described herein may additionally or alternatively include one or more of the features below. The container may include a longitudinal axis, at least one wall, and at least one blade disposed between the longitudinal axis and the wall. The container may have a longitudinal axis. The second passage may have a longitudinal axis. The longitudinal axis of the second passage may be parallel to or coaxial with the longitudinal axis of the container. The longitudinal axes of the container and the second passage may be coaxial. The second passage may extend into the container. The apparatus may include at least one helical groove and at least one protrusion movably disposed within the at least one helical groove. The at least one protrusion may move in the at least one helical groove during a transition between the first configuration and the second configuration. The apparatus may include a protrusion configured to prevent the passage of the powdered agent from the container to the second passage when the apparatus is in the first configuration. The second passage may comprise an opening. At least a portion of the protrusion may be inside the opening when the apparatus is in the first configuration. The protrusion may extend from a top wall of the container. The container may comprise a movable cap. The apparatus may transition from the first configuration to the second configuration upon twisting of the cap.

In another example, a method for providing a powdered agent to a target site may include delivering the powdered agent to the target site using an apparatus including a powder chamber housing the powdered agent, a catheter, and a chassis coupled to the powder chamber and the catheter. Delivering the powdered agent may include fluidizing the powdered agent by directing a flow of pressurized gas into the powdered agent. Delivering also may include transitioning the apparatus from a first configuration to a second configuration. The powder chamber and the catheter may not be in fluid connection in the first configuration and may be in fluid connection in the second configuration. Delivering also may include directing the fluidized powdered agent into the catheter. Delivering also may include emitting the fluidized powdered agent from a distal end of the catheter to the target site.

Any method described herein may include one or more of the features or steps described below. Rotating at least a portion of the powder chamber relative to the chassis. The powder chamber may include at least one helical groove and at least one protrusion movably disposed within the at least one helical groove. Rotating at least a portion of the powder chamber may cause the at least one protrusion to move within the at least one helical groove. In the second configuration, fluidized powdered agent may be able to enter a passage fluidly connecting the powder chamber to the catheter. The passage may be a tube extending into the powder chamber.

In yet another example, an apparatus for delivering a powdered agent into a subject's body may include a powder chamber housing the powdered agent and a chassis in fluid connection with the powder chamber. The chassis may include a first passage for receiving the powdered agent from the powder chamber. The chassis also may include a second passage in fluid connection with the first passage. The second passage may receive the powdered agent from the first passage for exiting the chassis. The apparatus also may include at least one agitator on at least one of the powder chamber and the chassis. The at least agitator may include at least one of a piston, an eccentric weight, a motor, a reed, or a pulsating valve.

Any apparatus for delivering a powdered agent into a subject's body may additionally or alternatively include one or more of the features described below. The chassis may further comprise a trigger and at least one gear. Depression of the trigger may cause movement of the at least one gear. The at least one gear may cause movement of a piston, such that the piston strikes a surface of the chassis. The chassis may further include a rotatable member having at least one trough for receiving the powdered agent and delivering the powdered agent to the first passage. The at least one trough may be helical.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings, which are incorporated in and constitute a part of this specification, illustrate aspects of the present disclosure and together with the description, serve to explain the principles of the disclosure.

FIGS. 14-18, 19A-19B, and 20-22 show powder and mixing chamber assemblies, in accordance with aspects of the present disclosure.

DETAILED DESCRIPTION

The present disclosure is drawn generally to apparatuses and methods for delivering powdered agents, and more specifically to apparatuses and methods for the endoscopic delivery of hemostatic powders. Reference now will be made in detail to aspects of the present disclosure, examples of which are illustrated in the accompanying drawings. Wherever possible, the same reference numbers will be used throughout the drawings to refer to the same or like parts. The term "distal" refers to a portion farthest away from a user when introducing an instrument into a subject. By contrast, the term "proximal" refers to a portion closest to the user when placing the instrument into the subject. Though the following description refers to "endoscope" or "endoscopy," the principles/aspects described herein may be used with any suitable introduction sheath or device, even if such sheath or device fails to include one or more features typically associated with "endoscopes." It may be understood that both the foregoing general description and the following detailed description are exemplary and explanatory only and are not restrictive of the features claimed. Further, as used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." The terms "substantially," "approximately" and "about" refer to a variation of plus or minus ten percent with respect to a stated value. The present embodiments disclosed herein may be used independently or in combination with one or more other disclosed embodiments.

Figure 1:
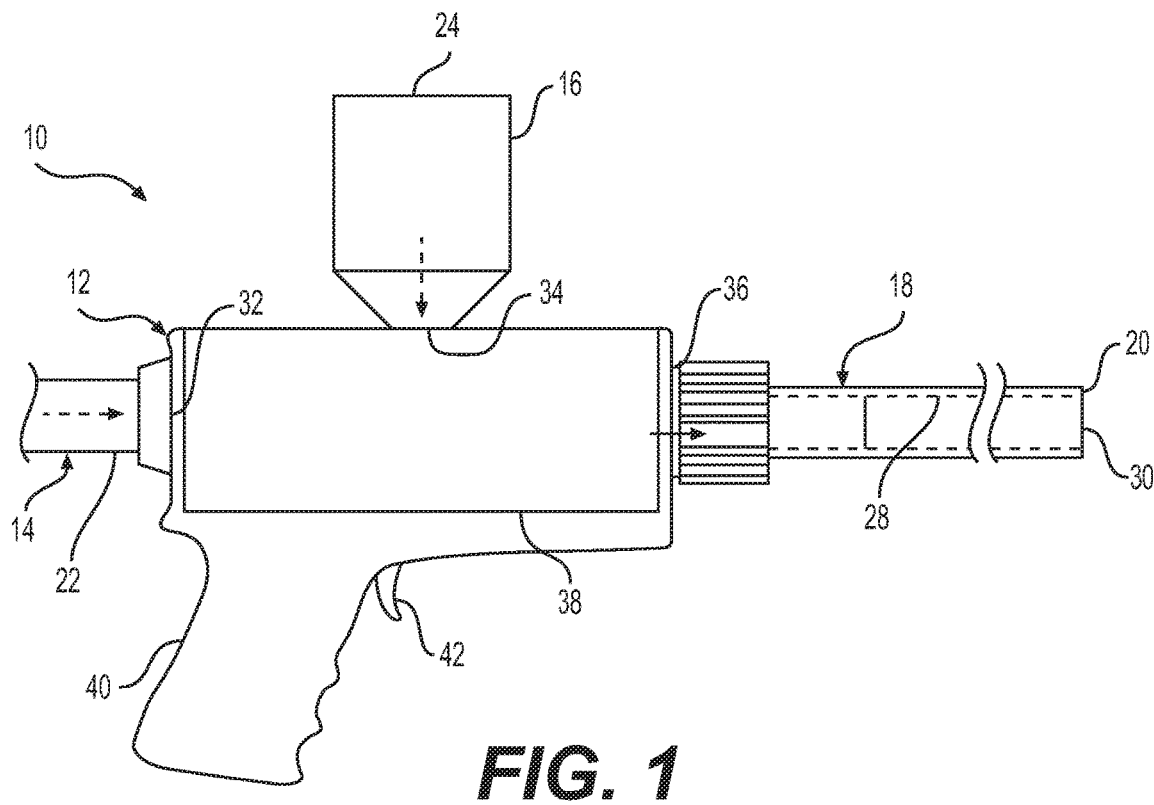
FIG. 1 shows an apparatus for delivering powdered agents, in accordance with aspects of the present disclosure.

FIG. 1 shows one example of an apparatus 10 for delivering powdered agents, in accordance with aspects of the present disclosure. Apparatus 10 may include, for example, a chassis 12, a gas supply 14 for supplying a pressurized gas to chassis 12, a powder chamber 16 for supplying a powdered agent 54 (FIG. 2) to chassis 12, and/or a catheter 18 for receiving a fluidized powdered agent from chassis 12. The fluidized powdered agent may include a mixture of the pressurized gas and the powdered agent. In one example, the pressurized gas may include air, and the powdered agent may include a hemostatic powder. The hemostatic powder may include, for example, particulate material that can stanch bleeding by initiating a coagulation cascade to clot a bleed, and/or a particulate material that can form a pseudo-clot upon coming into contact with blood due to hydrophilic properties of the powder.

During use with a subject (e.g., a patient), chassis 12, gas supply 14, and powder chamber 16 may remain outside of the subject, while catheter 18 may enter into the subject through, for example, an endoscope or other introducer sheath (not shown). In one contemplated use, catheter 18 may be inserted through the endoscope or sheath to position a distal end 20 of catheter 18 at or near a site of bleeding in the subject. The fluidized powdered agent may be emitted from the distal end 20 to the site to reduce or stop the bleeding.

Gas supply 14 may include, for example, a gas line 22. Gas line 22 may include a flexible length of tubing. A proximal end of gas line 22 may be coupled to a pressurized gas source (not shown), and a distal end of gas line 22 may be coupled to chassis 12, thereby creating a path for the pressurized gas to flow from the pressurized gas source to chassis 12. The pressurized gas source may include, for example, a pump device, a wall access in a hospital room, a canister, a manually-operated pump, a foot pedal-operated pump, and/or any other suitable pressurized gas source. Gas line 22 may be fixedly attached or removably attached to chassis 12 and/or the pressurized gas source.

Figure 2:
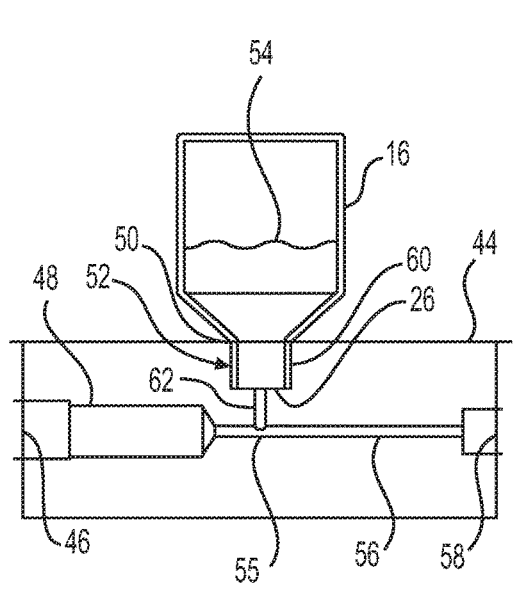
FIGS. 2-9 show powder and mixing chamber assemblies, in accordance with aspects of the present disclosure.

Powder chamber 16 may include any suitable receptacle for holding powdered agent 54. Powder chamber 16 may include, for example, a substantially rigid vessel, such as a bottle. Alternatively, powder chamber 16 may include a substantially flexible vessel, such as a bag. Powder chamber 16 may have a closed end 24 and an open end 26 (FIG. 2). Powdered agent 54 may pass through open end 26 on its way into chassis 12.

Powder chamber 16 may be fixedly attached or removably attached to chassis 12. Where powder chamber 16 is fixedly attached to chassis 12, reloading chassis 12 with powdered agent 54 may include removing a cap, cover, or the like from powder chamber 16, and pouring powdered agent 54 into powder chamber 16. Additionally or alternatively, reloading may entail switching out one or more components of chassis along with powder chamber 16. Where powder chamber 16 is removably attached to chassis 12, reloading chassis 12 with powdered agent 54 may include removing an empty powder chamber 16 from chassis 12, and coupling a full powder chamber 16 to chassis 12. Powder chamber 16 may be removably attached to chassis 12 by screw-type engagement, snap-fit engagement, friction fit engagement, and/or any other suitable form of attachment.

Catheter 18 may include a tubular length of medical grade material, and may have a proximal end with a proximal opening (not visible) and distal end 20 with a distal opening 30. The proximal end of catheter 18 may be coupled to chassis 12. Catheter 18 may include a lumen 28 extending therethrough from the proximal opening to distal opening 30. Fluidized powdered agent 54 from chassis 12 may flow through lumen 28 on its way to being emitted from distal opening 30. Catheter 18 may be sufficiently rigid to maintain its shape when inserted into the subject's body. Alternatively, catheter 18 may be sufficiently flexible to bend and conform to passages in the subject's body. Catheter 18 may be fixedly or removably attached to chassis 12.

Chassis 12 may include an inlet or port 32 to which gas line 22 may be coupled, an inlet or port 34 to which powder chamber 16 may be coupled, and an outlet or port 36 to which catheter 18 may be coupled. Chassis 12 may include a mixing chamber 38 that may be in fluid connection with inlet 32, inlet 34, and outlet 36. During use, the pressurized gas from gas line 22 may enter mixing chamber 38 via inlet 32, and powdered agent 54 may enter mixing chamber 38 via inlet 34. The pressurized gas and powdered agent 54 may mix in mixing chamber 38, producing fluidized powdered agent 54 that then exits from mixing chamber 38 and enters catheter 18 via outlet 36. Powdered agent 54 may be fluidized in that the pressurized gas may be introduced into powdered agent 54, resulting in the formation of a part-gas and part-solid medium having properties and characteristics of a fluid, such as a liquid.

Chassis 12 also may include a handle 40 for gripping by the user, and a trigger 42 for managing the flow of fluidized powdered agent 54. For example, trigger 42 may be operatively coupled to one or more valves (not shown) in one or more of inlet 32, inlet 34, mixing chamber 38, and outlet 36, to control the flow of one or more of the pressurized gas, powdered agent 54, and the fluidized powdered agent 54. Additionally or alternatively, trigger 42 may activate one or more actuators in apparatus 10 for facilitating fluidization of powdered agent 54. Exemplary actuators are described in the paragraphs below.

Mixing chamber 38 may be fixedly attached or removably attached to the rest of chassis 12. The removable attachment may be provided by any suitable mechanical attachment mechanism, such as by snap-fit engagement, friction fit, a latching mechanism, or the like. The removable attachment may allow the user to swap out one mixing chamber for another. FIGS. 2-22 show exemplary aspects of powder and mixing chamber assemblies. It is contemplated that any of the mixing chambers, powder chambers, and/or other chassis components, may be used in place of any other mixing chamber, powder chamber, and/or other chassis components. It also is contemplated that any aspect of any of the mixing chambers, powder chambers, and/or other chassis components, may be used in any of the other mixing chambers, powder chambers, and/or other chassis components.

FIG. 2 shows a powder chamber 16 with mixing chamber 44. Mixing chamber 44 may be used in place of mixing chamber 38 in FIG. 1. The same is true for other mixing chambers described below. Mixing chamber 44 may include an opening 46 and a passage 48 for the pressurized gas. The flow of pressurized gas through passage 48 and/or opening 46 may be controlled by any metering orifices. Mixing chamber 44 also may include an opening 50 and a passage 52 for powdered agent 54. Passage 48 and passage 52 may meet at a junction 55, where the pressurized gas may be introduced into powdered agent 54, thereby fluidizing powdered agent 54. Mixing chamber 44 also may include a passage 56 and an opening 58 for fluidized powdered agent 54. Any of the openings in mixing chamber 44 may have a circular shape. Any of the passages of mixing chamber 44 may have a circular cross-sectional shape. Other suitable opening shapes/cross-sectional shapes may be used, including, for example, polygonal and irregular shapes. It is contemplated that central longitudinal axes of passages 48 and 56 may be substantially aligned or coaxial. Additionally or alternatively, a central longitudinal axis of passage 52 may be transverse (e.g., substantially perpendicular or otherwise angled) to at least one of the central longitudinal axes of passages 48 and 56.

Passage 52 may include portions having different widths or diameters. For example, passage 52 may include a first portion 60 and a second portion 62. First portion 60 may be wider than second portion 62. The width, or diameter, of first portion 60 may be designed to receive open end 26 of powder chamber 16. Second portion 62, including its width or diameter, may be designed to control a rate of flow of powdered agent 54 into junction 55. Powder chamber 16 and passage 52 may be positioned above junction 55 such that gravity may assist with moving powdered agent 54 down from powder chamber 16 and passage 52 into junction 55.

FIGS. 3-5 depict exemplary configurations wherein one or more components may agitate powdered agent 54. Agitation may include, for example, acts of tapping, shaking, vibrating, pulsating, metering, and/or turbulization of powdered agent 54 and/or one or more components of an apparatus. While the below discussion makes reference to components of FIGS. 1 and 2, the examples discussed below may involve embodiments other than those depicted in FIGS. 1 and 2. The aspects described in FIGS. 3-5 may involve agitating component(s) of apparatus 10, for example, component(s) of chassis 12 and/or powder chamber 16. Such agitation may facilitate the movement of powdered agent 54 through, for example, open end 26, opening 50, and/or passage 52. Movement of powdered agent 54 may be facilitated into, for example, passage 56 and/or junction 55.

FIG. 3 shows a mixing chamber 64. Mixing chamber 64 may include components that are the same or similar to those in mixing chamber 38 and/or mixing chamber 44 as described with regard to FIGS. 1 and 2 above. Mixing chamber 64 may include one or more striker assemblies 66. A striker assembly 66 may be any type of device which may move so as to strike a surface. For example, striker assembly 66 may include an actuator 63, a rod 65, a piston 67, and a component 68. Actuator 63 may be configured to move rod 65 and piston 67 in a reciprocating manner to strike one or more surfaces of component 68. Actuator 63 may include a motor, a pneumatic actuator, a hydraulic actuator, and/or any other suitable actuator. Actuator 63 may be powered by pressurized gas from line 22, and/or by a mechanical or electrical power source. Component 68 may include, for example, a bracket, a housing, a recess or cavity, and/or any other structure that is part of or affixed to mixing chamber 64, with one or more of its surfaces capable of being struck by piston 67. In one example, the crown of piston 67, and the surface of piston 67 opposite the crown, may repeatedly strike opposing surfaces at opposite ends of component 68 to agitate apparatus 10.

In the example shown in FIG. 3, striker assembly 66 is mounted on a lower surface of passage 56 and/or passage 48, below junction 55. Other positions and/or orientations also are contemplated. For example, one or more striker assemblies 66 may be mounted on any of the interior and/or exterior surfaces of powder chamber 16, mixing chamber 64, and/or the rest of chassis 12, including on surfaces defining passage 48, passage 52, passage 56, and/or junction 55. Striker assembly 66 may be oriented so that piston 67 travels in a direction parallel to a surface on which striker assembly 66 is provided. In the alternative, striker assembly 66 may be oriented so that piston 67 travels in a direction perpendicular, or otherwise angled, relative to the surface on which striker assembly 66 is provided.

Piston 67 may be actuated to move when it is desired that powdered agent 54 be delivered. For example, piston 67 may move when trigger 42 is depressed. The action of piston 67 may agitate mixing chamber 64, powder chamber 16, or another component of chassis 12 and/or apparatus 10. Such agitation may result in powdered agent 54 moving through a portion of apparatus 10 such as open end 26, opening 50, and/or passage 52. It is contemplated that, due to the consistency and repeatability of the movements of piston 67, a predetermined amount of powdered agent 54 may be dispensed into junction 55 and/or passage 52 based on operation of piston 67. The predetermined amount may be set by adjusting, for example, a frequency of actuator 63, and/or a force applied by actuator 63 on rod 65 and piston 67.

Figure 4:
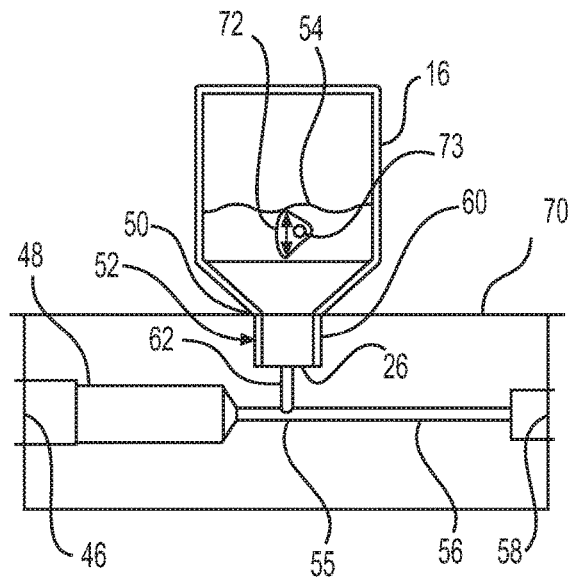

FIG. 4 shows powder chamber 16 with a mixing chamber 70. Powder chamber 16 may include one or more weights 72. A weight 72 may include an eccentric weight, and may be of any suitable shape and size. Weight 72 may be mounted on, within, or near any component of apparatus 10, such as powder chamber 16, mixing chamber 70, and/or another portion of chassis 12. In the example shown in FIG. 4, weight 72 is mounted on an exterior surface of powder chamber 16. Additionally or alternatively, weight 72 may be mounted on an interior surface of powder chamber 16, and/or on interior and/or exterior surfaces of mixing chamber 70 and/or another portion of chassis 12.

Weight 72 may move relative to apparatus 10. Weight 72 may be configured to move when it is desired that powdered agent 54 be delivered. For example, weight 72 may move when trigger 42 is depressed. Any suitable actuator (not shown), such as a motor, turbine, or other suitable rotational drive, may spin weight 72. The actuator may be powered by the pressurized gas from line 22 and/or a mechanical or electrical power source. Weight 72 may spin on a rotational axis 73. Weight 72, and due to its eccentricity, may agitate mixing chamber 70, powder chamber 16, or another component of chassis 12 and/or apparatus 10. Such agitation may result in powdered agent 54 moving more readily through apparatus 10.

Figure 5:
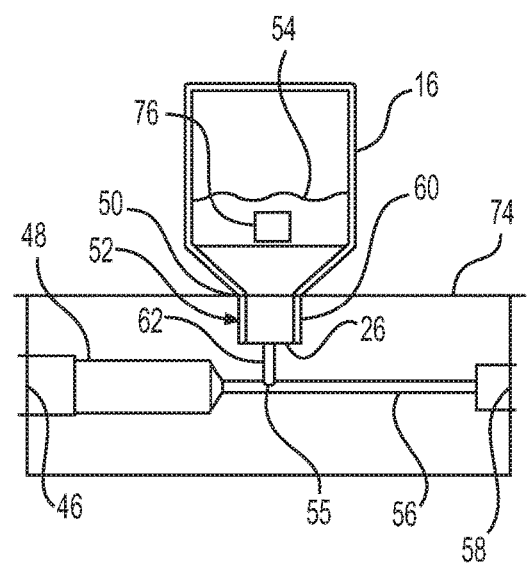

FIG. 5 shows powder chamber 16 with a mixing chamber 74. One or more motors 76 may be mounted on, within, or near any component of apparatus 10, such as powder chamber 16, mixing chamber 74, and/or another portion of chassis 12 and/or apparatus 10. Motor 76 may be mounted on any of the interior and/or exterior surfaces of powder chamber 16, mixing chamber 74, and/or chassis 12 and/or apparatus 10. Motor may be powered by pressurized gas from line 22, and/or any suitable mechanical or electrical power source.

Motor 76 may be configured to operate when it is desired that powdered agent 54 be delivered. For example, motor 76 may operate when trigger 42 is depressed. The operation of motor 76 may cause motor 76 to vibrate, resulting in agitation of mixing chamber 74, powder chamber 16, and/or another component of chassis 12 and/or apparatus 10. Such agitation may result in powdered agent 54 moving more fluidly through apparatus 10.

Figure 3:
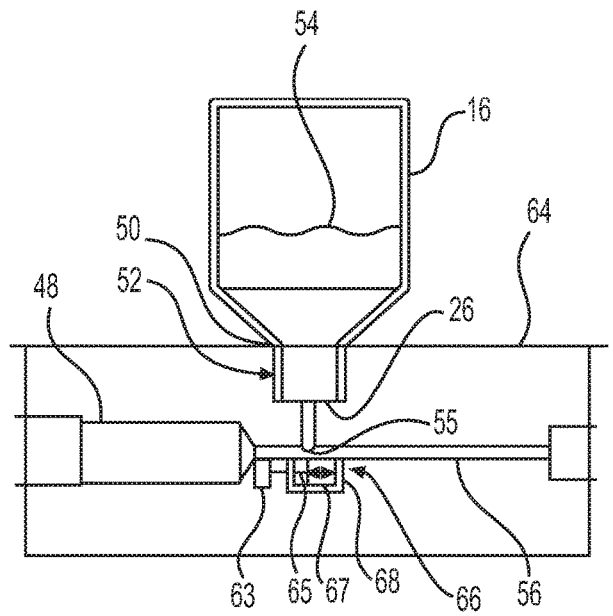
Figure 6:
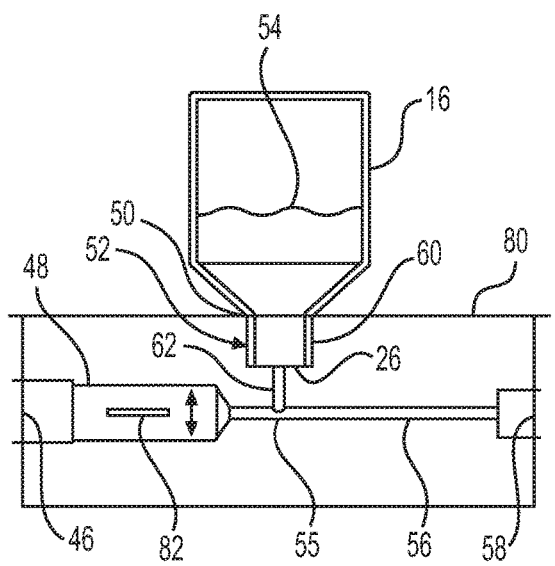
Figure 7:
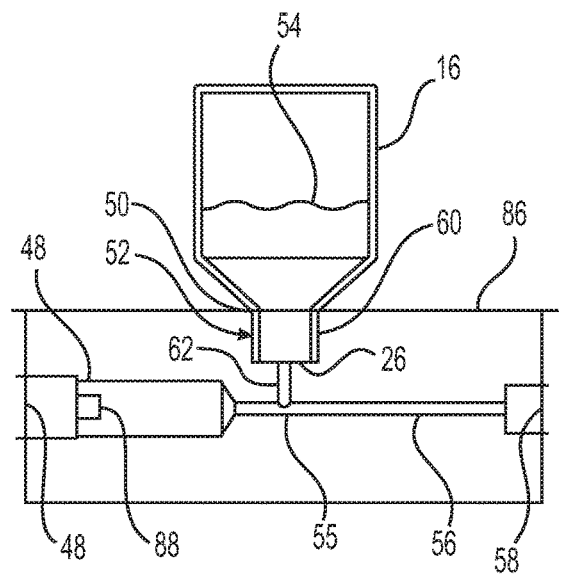

FIGS. 6-7 depict exemplary configurations wherein components may agitate powdered agent 54 via turbulent flow of pressurized gas. While the below discussion makes reference to components of FIGS. 1-2, the examples discussed below may involve apparatuses other than those depicted in FIGS. 1-2. The examples of FIGS. 6-7 may also include features of FIGS. 3-5 involving the use of mechanical movement of powder chamber 16, chassis 12, or another component of apparatus 10 to agitate powdered agent 54. Such turbulent gas flow and/or mechanical movement may facilitate the movement of powdered agent 54 through apparatus 10.

FIG. 6 shows powder chamber 16 with a mixing chamber 80. Mixing chamber 80 may include one or more reeds 82. A reed 82 may be comprised of, for example, a piece of thin cane, metal, or synthetic material, either single or doubled, that may vibrate when in a current of pressurized gas. Reed 82 may be an idioglottal reed or a heteroglottal reed. Reed 82 may be a single reed or a multiple reed (e.g., a double reed). Reed 82 may be, for example, similar to a reed used in a musical instrument.

Reed 82 may have a longitudinal axis. Reed 82 may be located at least partially in, for example, opening 46, passage 48, passage 56, and/or opening 58 of mixing chamber 80. Reed 82 may have a longitudinal axis and may be aligned such that a longitudinal axis of reed 82 is parallel to a longitudinal axis of passage 48 and/or passage 56. In the alternative, a longitudinal axis of reed 82 may be disposed at an angle relative to a longitudinal axis of passage 48 and/or passage 56. A longitudinal axis of reed 82 may align with the center of, for example, opening 46, passage 48, passage 56, and/or opening 58. In the alternative, a longitudinal axis of reed 82 may be disposed off-center with respect to a longitudinal axis of, for example, opening 46, passage 48, passage 46, and/or opening 58. Reed 82 may be secured in the desired location by any suitable mechanism (not depicted). It is contemplated that one end of reed 82 may be secured, while the opposite end of reed 82 may be free to move when exposed to a current of pressurized gas.

Reed 82 may be disposed so that pressurized gas passing through opening 46 may flow around reed 82, causing reed 82 to oscillate or otherwise vibrate. The movement of reed 82 may cause turbulence in the flow of gas through, for example, opening 46, passage 48, passage 56, or opening 58. The movement of reed 82 may also agitate one or more components of apparatus 10, including chassis 12, mixing chamber 80, and/or powder chamber 16. Such turbulence and/or vibration may facilitate the movement of powdered agent 54 through apparatus 10.

FIG. 7 shows powder chamber 16 with a mixing chamber 86. Mixing chamber 86 may include one or more valves 88. A valve 88 may be a pulsating valve. Valve 88 may be located in, for example, opening 46, passage 48, passage 56, and/or opening 58. The actuation of valve 88 may cause turbulence in the flow of gas through, for example, opening 46, passage 48, passage 56, and/or opening 58. The actuation of valve 88 may also agitate one or more components of apparatus 10, including chassis 12, mixing chamber 86, and/or powder chamber 16. Such turbulence and/or vibration may be generated by valve 88 moving between an open state, allowing puffs of pressurized gas to flow therethrough, and a closed state, blocking pressurized gas from flowing therethrough, and to states in between open and closed. In one example, valve 88 may move between states in repeating cycles, and with a frequency that produces the agitation. Actuation of valve 88 between states may be driven by the pressurized gas, and/or any suitable mechanical or electrical power source. The agitation may facilitate the movement of powdered agent 54 through apparatus 10.

FIG. 8 shows powder chamber 16 with a mixing chamber 90. Mixing chamber 90 may include a mechanism 91. Mechanism 91 may include, for example, a trap door. Mechanism 91 may be planar or may have any other suitable shape. Mechanism 91 may be configured so that a surface of mechanism 91 is transverse (e.g., perpendicular) to a longitudinal axis of passage 52, and/or parallel to a longitudinal axis of passage 48 and/or passage 56. Mechanism 91 may be located near junction 55. For example, mechanism 91 may be located at the end of passage 52 nearest to junction 55. Alternatively, mechanism 91 may be located in any portion of passage 52. Mechanism 91 may also be located at, for example, open end 26 or opening 50.

Mechanism 91 may be configured to transition between an open state and a closed state. For example, mechanism 91 may slide back and forth along an axis perpendicular to the axis of passage 52. Mechanism 91 may also be configured so that mechanism 91 may transition between an open state where a plane of mechanism 91 is perpendicular to an axis of passage 52, and a closed state where a plane of mechanism 91 is parallel to an axis of passage 52, or is at another angle relative to an axis of passage 52. For example, mechanism 91 may include a door configured to swing on a hinge. Mechanism 91 may be configured so as to, in a first configuration, cover open end 26 or opening 50, and in a second configuration, leave open end 26 or opening 50 open. Mechanism 91 may transition between the open and closed states by way of, for example, any suitable sliding mechanism or a hinge.

Figure 8:
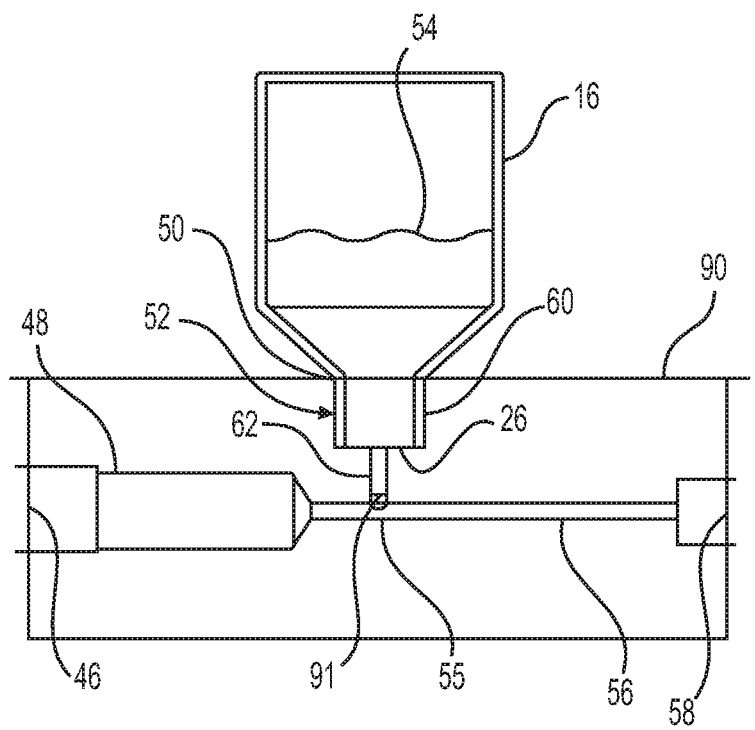

Mechanism 91 may be configured to be in the open and/or closed states for a predetermined amount of time. For example, mechanism 91 may be configured to be in the open state for a predetermined amount of time to allow a predetermined amount of powdered agent 54 to pass by mechanism 91. Mechanism 91 may also be configured to rapidly transition between the open state and the closed state. Such a rapid transition may be optimized for passage of powdered agent 54 past mechanism 91. The transition of mechanism 91 between the open state and the closed state may agitate mixing chamber 90, powder chamber 16, chassis 12, and/or another component of apparatus 10. Such agitation may result in powdered agent 54 moving through a portion of apparatus 10 such as open end 26, opening 50, and/or passage 52. Additionally or alternatively, mechanism 91 may engage packed bodies of powdered agent 54, and break them apart, as it moves between the open and closed states. As with the other configurations disclosed herein, the configuration of FIG. 8 may be used alone or in combination with any of the examples discussed above or below.

Figure 9:
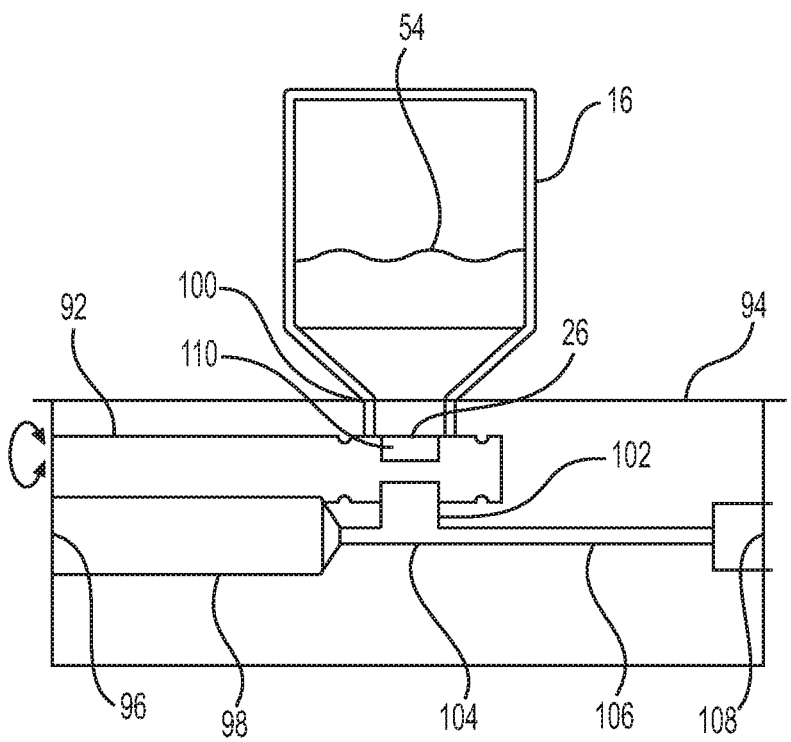

As shown in FIGS. 9-12, a metering device 92 may be used to agitate powdered agent 54 and/or dispense predetermined quantities of powdered agent 54. FIG. 9 shows powder chamber 16 with a mixing chamber 94. Mixing chamber 94 may be configured similarly to any of the aforementioned mixing chambers. Mixing chamber 94 may include an opening 96 and a passage 98 for receiving and channeling a flow of pressurized gas. Mixing chamber 94 also may include an opening 100 and a passage 102 for receiving and channeling powdered agent 54. Passage 98 and passage 102 may meet at a junction 104, where the pressurized gas may be introduced into powdered agent 54, thereby fluidizing powdered agent 54. Mixing chamber 94 also may include a passage 106 and an opening 108 for receiving and channeling fluidized powdered agent 54.

Mixing chamber 94 may include metering device 92. Metering device 92 may be rotatably received in a hole in mixing chamber 94. Metering device 92 may have a longitudinal axis which is parallel or substantially parallel to passages 98 and 106, and/or perpendicular or substantially perpendicular to passage 102. Metering device 92 may be configured so as to pass through passage 102 or to pass between passage 102 and junction 104. Metering device 92 may include one or more recesses or cavities, including, for example, alcoves 110. Alcoves 110 may be of a number of shapes, as discussed in further detail below.

In operation, metering device 92 may be rotated about its central longitudinal axis so that alcoves 110 also rotate around the central longitudinal axis of metering device 92. Alcoves 110 may be below powder chamber 16 and/or opening 100 so that powdered agent 54 may flow into an alcove 110. As the metering device 92 rotates, one alcove 110 may rotate toward the bottom of mixing chamber 94 and another alcove 110 may rotate toward the top of mixing chamber 94. Thus, an amount of powdered agent 54 may enter alcove 110 that is rotated toward the top. Once metering device 92 has been rotated further, bringing the powdered agent 54 containing alcove 110 toward the bottom of mixing chamber 94, gravity may cause the powdered agent in alcove 110 to fall or otherwise move from alcove 110 to junction 104 or passage 106. Meanwhile, powdered agent 54 may flow into another alcove 110 of metering device 92 that has been brought to the top by the rotation of metering device 92. Thus, turning of metering device 92 may facilitate repeatable dispensing of a predetermined amount of powdered agent 54, corresponding to the volume of alcove 110 and the speed of rotation of metering device 92, into junction 104 or passage 106. Metering device 92 may therefore aid in dispensing a predetermined amount of powdered agent 54 out of opening 108 and/or may assist in developing an even flow of powdered agent 54 out of opening 108.

Figure 10:
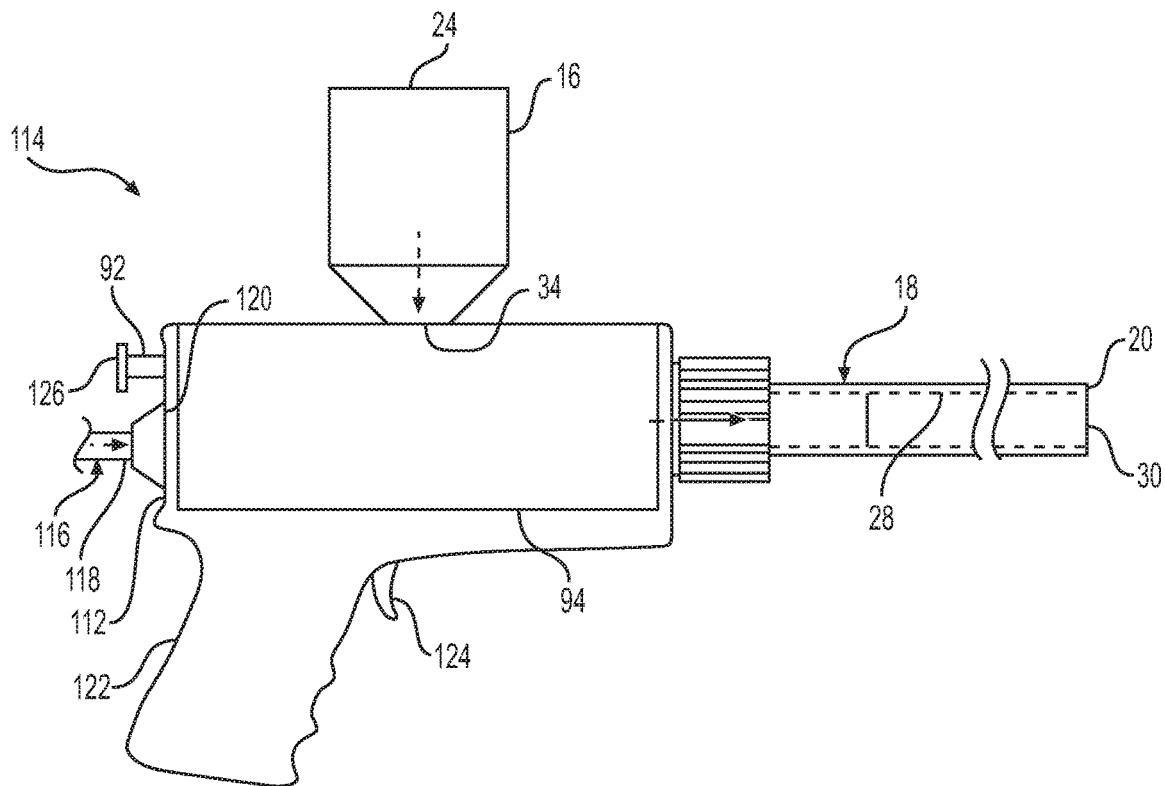
FIG. 10 shows an apparatus for delivering powdered agents, in accordance with aspects of the present disclosure.

As shown in FIG. 10, metering device 92 may extend out of an end of mixing chamber 94 and through a chassis 112 of an apparatus 114. Chassis 112 and apparatus 114 may be the same as, or similar to, chassis 12 and apparatus 10, respectively (FIG. 1). Chassis 112 and apparatus 114 may include any of the features of chassis 12 and apparatus 10, respectively. For example, apparatus 114 may include a gas supply 116, which may be the same as or similar to gas supply 14. Gas supply 116 may include, for example, a gas line 118, which may be the same as or similar to a gas line 22.

Chassis 112 may include an inlet or port 120 (which may be the same as or similar to inlet or port 32) to which gas line 118 may be coupled. Chassis 112 may receive mixing chamber 94, or any of the other mixing chambers described herein. Mixing chamber 94 may be in fluid connection with inlet 120. During use, the pressurized gas from gas line 118 may enter mixing chamber 94 via inlet 120. Pressurized gas and powdered agent 54 may mix in mixing chamber 94, producing fluidized powdered agent 54 that then exits from mixing chamber 94.

Chassis 112 also may include a handle 122 (which may be the same as or similar to handle 40) for gripping by the user, and a trigger 124 (which may be the same as or similar to trigger 42) for managing the flow of fluidized powdered agent 54. Mixing chamber 94 may be fixedly attached or removably attached to the rest of chassis 112.

Metering device 92 may pass through chassis 112, for example near inlet or port 120. Metering device 92 may include a handle or knob 126 by which metering device 92 may be rotated. Alternatively, metering device 92 may include components (e.g., any suitable actuator) allowing for automatic rotation of metering device 92.

Figure 11:
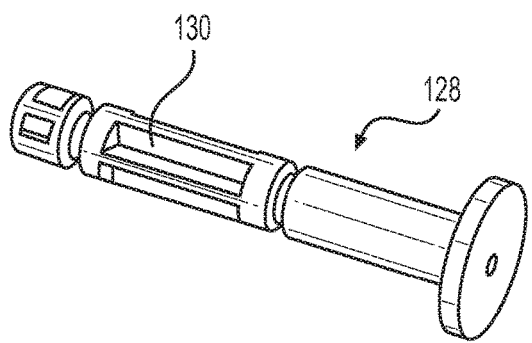
FIGS. 11-12 show metering devices, in accordance with aspects of the present disclosure.

FIG. 11 depicts a metering device 128, which may be a configuration of metering device 92. Metering device 128 includes one or more cavities, recesses, or alcoves in the form of troughs 130. Troughs 130 may have a triangular cross section, a rectangular cross section, a semicircular cross section, or any other suitable cross-section such as a polygonal cross section. Troughs 130 may have boundary walls between them which are relatively narrow so that powdered agent 54 may dispense evenly into troughs 130. Troughs 130 may have an elongate shape with a uniform cross-sectional shape throughout their length. Troughs 130 may also have a changing cross-sectional shape throughout their length. The length of troughs 130 may be roughly the same as the width of, for example, passage 102 as depicted in FIG. 9. Alternatively, troughs 130 may be longer than the width of 102. Troughs 130 may be designed so as to allow an optimized or otherwise predetermined amount of powdered agent 54 to pass from powder chamber 16 to a mixing chamber such as mixing chamber 94, as depicted in FIG. 9, in a given time, based on the frequency of rotation of metering device 128.

Figure 12:
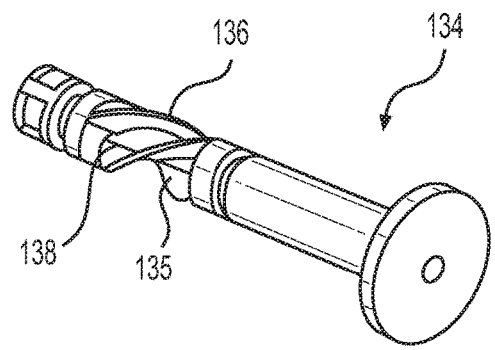

FIG. 12 depicts a metering device 134, which may be a configuration of a metering device 92. Metering device 134 may include an auger 135 with helically shaped blades 136 which create helically shaped recesses, cavities, or alcoves therebetween, including, for example, containers 138 into which powdered agent 54 may enter and exit. Auger 135 may allow an optimized or otherwise predetermined amount of powdered agent 54 to pass from powder chamber 16 to a mixing chamber such as mixing chamber 94 as depicted in FIG. 9 in a given time, based on the frequency of rotation of metering device 134. Auger 135 also may allow for continuous delivery of powdered agent 54 into the pressurized air stream due to the intertwining arrangement of containers 138. It also is contemplated that any surfaces of metering device 92 may break apart packed bodies of powdered agent 54 to further facilitate movement of powdered agent 54 through apparatus 114.

Figure 13:
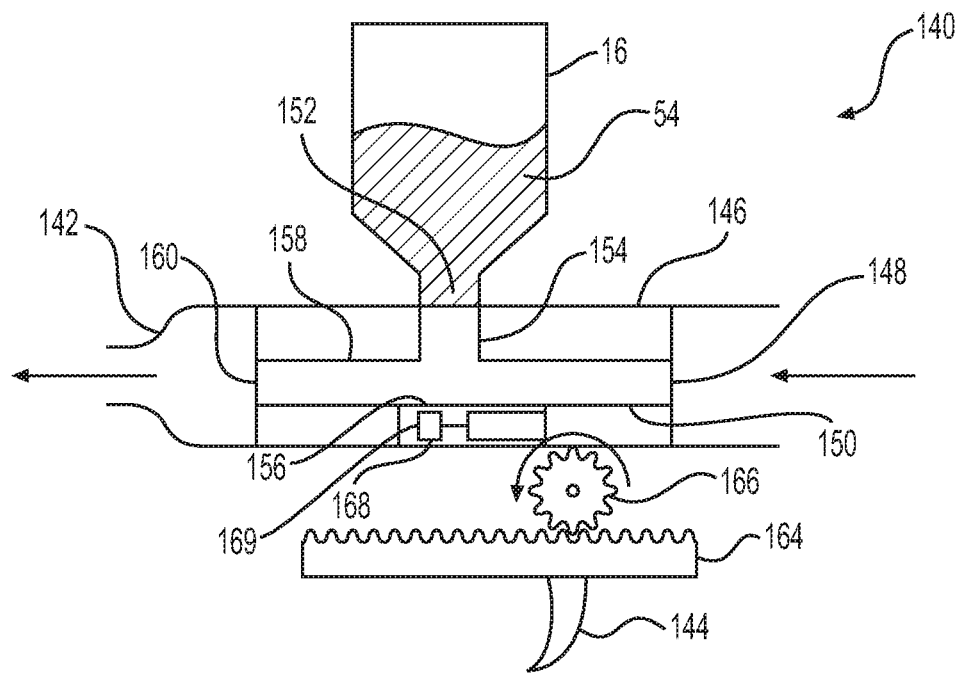
FIG. 13 shows an apparatus for delivering powdered agents, in accordance with aspects of the present disclosure.
Figure 14:
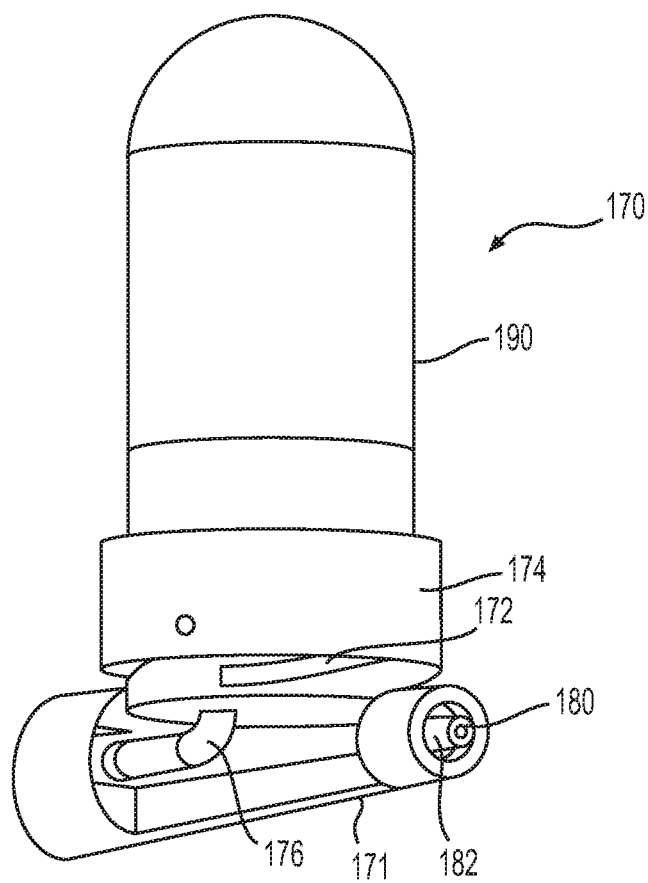

FIG. 13 depicts an example of an apparatus 140 for delivering powdered agents, in accordance with aspects of the present disclosure. Apparatus 140 may be the same as or similar to apparatus 10 depicted with regard to FIG. 1. Apparatus 140 may include any of the features described with regard to apparatus 10. For example, apparatus 140 may include a chassis 142. Chassis 142 may include a mixing chamber 146. Chassis 142 may also include a trigger 144 for managing the flow of fluidized powdered agent 54. Trigger 144 may be operatively connected to components of apparatus 140 as described with regard to trigger 42 with regard to FIG. 1. Mixing chamber 146 may be fixedly attached or removably attached to the rest of chassis 142.

Mixing chamber 146 may include an opening 148 and a passage 150 for the pressurized gas. Mixing chamber 146 also may include an opening 152 and a passage 154 for powdered agent 54. Passage 150 and passage 154 may meet at a junction 156, where the pressurized gas may be introduced into powdered agent 54, thereby fluidizing powdered agent 54. Mixing chamber 146 also may include a passage 158 and an opening 160 for fluidized powdered agent 54.

Chassis 142 may include a trigger 144. Trigger 144 may be the same as or similar to trigger 42 and may manage the flow of fluidized powdered agent 54. Trigger 144 may engage one or more gears. For example, depression of trigger 144 may cause movement of one or more gears 164. Gear 164 may, for example, be a straight gear (e.g., a gear rack) configured to move along a linear path. Alternatively, gear 164 may be a round gear or a gear of any other shape. Gear 164 may interact with one or more other gears 166. Gear 166 may be, for example, a round gear configured to rotate about a rotational axis. Alternatively, gear 166 may be of any other shape. Additional gears may also interact with gears 164 and 166.

The movement of gears 164 and/or 166 may actuate one or more pistons 168. Piston 168 may be the same or similar to piston 67. Depression of trigger 144 and/or movement of gears 164 and/or 166 may cause movement of a crown of one or more pistons 168. A piston 168 may be any type of piston which may move so as to strike a surface of apparatus 140. For example, a crown of piston 168 may strike a surface of a recess or cavity 169, or a housing (not shown) similar to component 68 of FIG. 3, of mixing chamber 146. Additionally or alternatively, piston 168 may be configured to come into contact with powder chamber 16 and/or a portion of chassis 142 other than mixing chamber 146. Piston 168 may be configured to move in a proximal-distal direction, or alternatively, in a direction perpendicular to, or otherwise angled relative to, the proximal-distal direction.

The action of piston 168 may agitate mixing chamber 146, powder chamber 16, or another component of apparatus 140. Such agitation may result in powdered agent 54 moving more easily through apparatus 140. Piston 168, chassis 142, and mixing chamber 146 may be configured to dispense a predetermined amount of powdered agent 54 based on the frequency of movement, and/or the force of movement, of piston 168.

Trigger 144, gear 164 and/or gear 166 may be configured so that, upon release of trigger 144, trigger 144, gear 164, and/or gear 166 will return to the position they were in prior to depression of trigger 144. For example, one or more springs (not shown), or other suitable biasing members, may be used to return trigger 144, gear 164, and/or gear 166 to their rest positions. The return of trigger 144, gear 164, and/or gear 166 to their rest positions may be damped.

FIGS. 14-17 depict an assembly 170 of a powder chamber 190 and a mixing chamber 171. Assembly 170 may be used in conjunction with chassis 12 as depicted in FIG. 1, in place of powder chamber 16 and mixing chamber 38. In the alternative, assembly 170 may be used in place of any of the other powder and mixing chamber assemblies described herein.

Powder chamber 190 may include any suitable receptacle for holding powdered agent 54. Powder chamber 190 may include, for example, a substantially rigid vessel, such as a bottle. Powder chamber 190 may be fixedly attached or removably attached to any suitable chassis, such as chassis 12 or any other aforementioned chassis. In FIG. 14, powder chamber 190 is fixedly attached to mixing chamber 171. Reloading assembly 170 with powdered agent 54 may include removing a cap, cover, or the like from powder chamber 190, and pouring powdered agent 54 into powder chamber 190, or swapping out an empty assembly 170 for a full assembly 170. Where powder chamber 190 is removably attached to mixing chamber 171, reloading may include removing an empty powder chamber 190 from mixing chamber 171, and coupling a full powder chamber 190 to mixing chamber 171.

As shown in FIG. 14, mixing chamber 171 may include one or more helical grooves 172. Powder chamber 190 may include one or more radially-inwardly-extending protrusions or threads 206 (see FIG. 15) slidably received in the one or more helical grooves 172. As powder chamber 190 is rotated in a first direction (e.g., a clockwise direction), engagement between protrusions 206 and the one or more helical grooves 172 may move powder chamber 190 downward toward mixing chamber 171. As powder chamber 190 is rotated in a second direction (e.g., a counterclockwise direction) opposite the first direction, engagement between the protrusions and the one or more helical grooves 172 may move powder chamber 190 upward away from mixing chamber 171.

Powder chamber 190 may include a base or wider portion 174. Wider portion 174 may serve as a gripping portion for a user to rotate powder chamber 190. Mixing chamber 171 may include a passage 176 for directing pressurized gas into powder chamber 190. Mixing chamber 171 may also include an opening 180 and a passage 182, wherein passage 182 may direct fluidized powdered agent 54 to opening 180 and out of mixing chamber 171.

FIG. 15 depicts a cross-section of assembly 170 in a closed position that restricts the flow of fluidized powdered agent 54. Assembly 170 may include an opening 184 in mixing chamber 171 for allowing pressurized gas to enter passage 176. Passage 176 may include a wider portion 186 for receiving the pressurized gas, and a narrower portion 188 for concentrating the pressurized gas into a smaller volume, thereby increasing its energy. The flow of pressurized gas through opening 184 and/or passage 176 may also be included by metering orifices placed in any suitable location. Pressurized gas may enter powder chamber 190 through an opening 192. Opening 192 may be at the bottom of powder chamber 190, on a top surface of mixing chamber 171. Powder chamber 190 may contain powdered agent 54. The pressurized gas exiting opening 192 may fluidize powdered agent 54 within powder chamber 190. While FIG. 15 depicts narrower portion 188 extending vertically toward opening 192, it also is contemplated that narrower portion 188 may extend at an angle toward opening 192, such that narrower portion 188 may be tilted from the orientation shown in FIG. 15. Additionally or alternatively, narrower portion 188 may extend along a helical path to opening 192. This may result in the pressurized gas being introduced into powder chamber 190 in the form of a swirling vortex, to fluidize powdered agent 54. The interior surface of narrower portion 188 may also include protrusions or other surface texture to cause turbulence or a vortex in the pressurized gas.

Assembly 170 may also include passage 194. Passage 194 may include a top opening 196. Passage 194 may be in fluid connection with passage 182. Passage 194 may have a longitudinal axis which is coaxial with, or parallel to, a longitudinal axis of powder chamber 190. Powder chamber 190 may also include a protrusion 198 extending downwardly from a top portion of an outer wall 200. Protrusion 198 may have a lower portion 202 with a cross section narrower than opening 196. Protrusion 198 may taper so that an upper portion 204 of protrusion 198 has a cross section wider than opening 196. Protrusion 198 may be aligned with passage 194 so that lower portion 202 of protrusion 198 may enter passage 194 via opening 196, thereby plugging opening 196, either partially or fully depending on the depth of insertion of lower portion 202 into passage 194, to put assembly 170 in the closed position (FIG. 15).

FIG. 16 depicts a cross section of assembly 170 in an open position that may allow fluidized powdered agent 54 to flow. To transition assembly 170 from the closed position to the open position, powder chamber 190 may be rotated relative to mixing chamber 171. Such rotation may cause movement of one or more protrusions or threads 206 in helical grooves 172. Powder chamber may thus be moved upward. Protrusion 198 may move upward so that lower portion 202 is no longer inside of passage 194, or so that protrusion 198 is otherwise not blocking opening 196. Passage 194 may be in fluid connection with the interior of powder chamber 190 and passage 176 when assembly 170 is in the open position. When powder chamber 170 is the open position, fluidized powdered agent 54 may thus enter opening 196, pass through passage 194, and eventually pass through passage 182 and out opening 180.

One or more curved surfaces a top portion of powder chamber 190, in conjunction with the tapering surfaces of protrusion 198, may funnel or otherwise facilitate flow of fluidized powder agent 54 toward a central longitudinal axis of powder chamber 190, and toward opening 196 of passage 194. For example, the curved surfaces and the tapering surfaces of protrusion 198 may form a portion of a toroid. Side walls of powder chamber 190 may be tapered, such that powder chamber gets narrower as it extends upward, to help direct fluidized powder agent 54 into passage 194.

It also is contemplated that assembly 170 may have a plurality of open positions that allow different levels of flow of fluidized powdered agent 54 through passage 194. For example, the greater the distance between protrusion 198 and opening 196, the greater the flow of fluidized powdered agent 154 into opening 196. Decreasing the distance may reduce the flow, while still allowing flow at the reduced level.

FIG. 17 shows an alternative arrangement of an assembly 210 similar to assembly 170. A powder chamber 211 of assembly 210 may include a removable cap 212. An upper portion of powder chamber 211 may have one or more helical grooves 214 on its exterior. Cap 212 may have a wider bottom portion 216 configured to receive the upper portion of powder chamber 211. Cap 212 may be rotated relative to the upper portion of powder chamber 211 to transition assembly 210 from a closed position similar to that shown in FIG. 15, to an open position similar to that shown in FIG. 16. Bottom portion 216 or another portion of cap 212 may include one or more protrusions or threads (not shown), similar to one or more protrusions/threads 206 (FIG. 15), which fit in helical groove 214 and facilitate moving cap 212 from a lower, closed position to a raised, open position. The operation of assembly 210 may be similar to that as explained for assembly 170 as described with regard to FIGS. 14-16.

FIG. 18 shows an alternative configuration of an assembly including a mixing chamber, such as mixing chamber 171, and a powder chamber, such as powder chamber 190 or powder chamber 211. The features of exemplary aspects depicted in FIG. 18 will be described with regard to assembly 170, but any of the other assemblies described herein may be used in conjunction with the features of FIG. 18. As shown in FIG. 18, assembly 170 may include a fluid randomizer 220. Fluid randomizer 220 may have one or more blades 222 extending between an inner ring 224 and an outer ring 226. Blades 222 may be planar or may have any other suitable shape. For example, blades 222 may be curved and/or may be angled. Blades 222 may have a solid surface area or may have a surface area with holes or other voids. Randomizer 220 may be configured so as to distribute the flow of pressurized gas and/or fluidized powdered agent 54 within container 190. For example, randomizer 220 may cause pressured gas and/or fluidized powdered agent 54 to flow more evenly within powder chamber 190. Such even flow may facilitate movement of fluidized powder 54 toward opening 196 of passage 194.

In one example, inner ring 224 of fluid randomizer 220 may extend concentrically around passage 194. An inner surface of inner ring 224 may be in contact with an outer surface of passage 194. Additionally or alternatively, outer ring 226 of fluid randomizer 222 may extend about an interior surface of powder chamber 190. An outer surface of outer ring 226 may be in contact with the interior surface of powder chamber 190. It is contemplated that inner ring 224 may be fixedly coupled to passage 194, and/or outer ring 226 may be fixedly coupled to the interior surface of powder chamber 190. Alternatively, inner ring 224 may be movably (e.g., slidably) coupled to passage 194, and/or outer ring 226 may be movably (e.g., slidably) coupled to the interior surface of powder chamber 190, allowing fluid randomizer 220 to move (e.g., rotate and/or rise and fall) within powder chamber 190. Movement of fluid randomizer 220 may be driven by the pressurized gas entering powder chamber 190 via opening 192.

Figure 18:
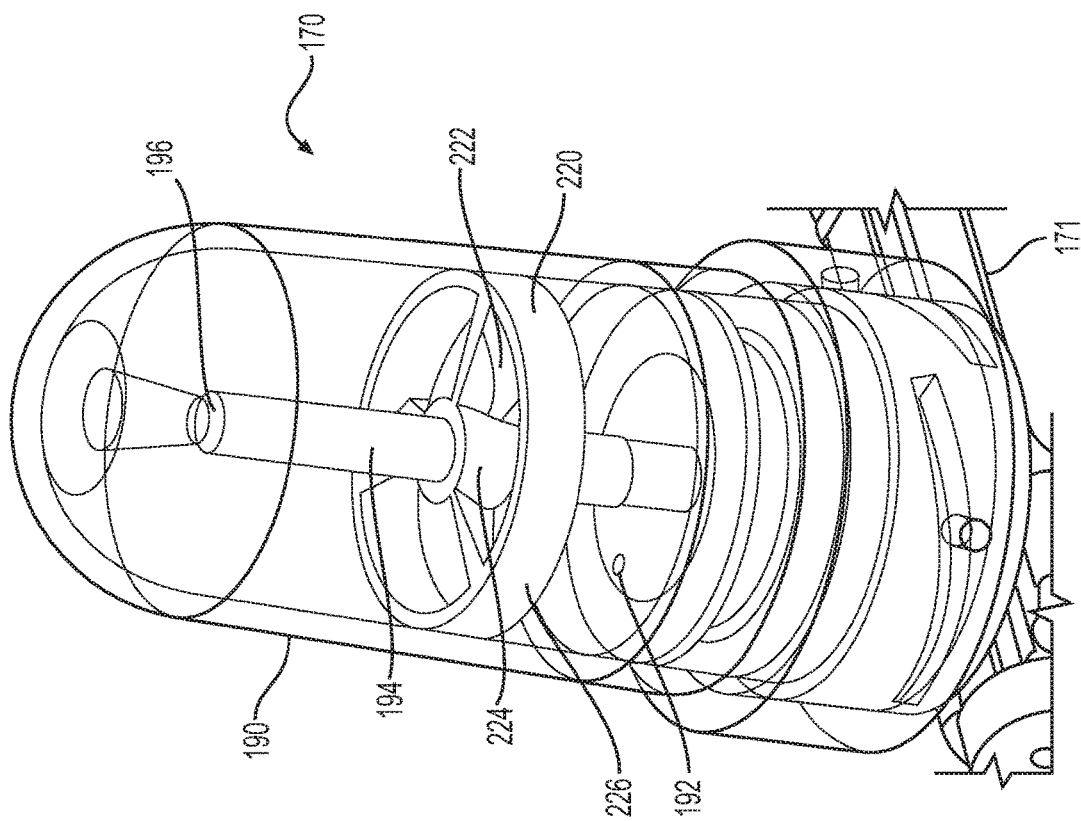
Figure 19A:
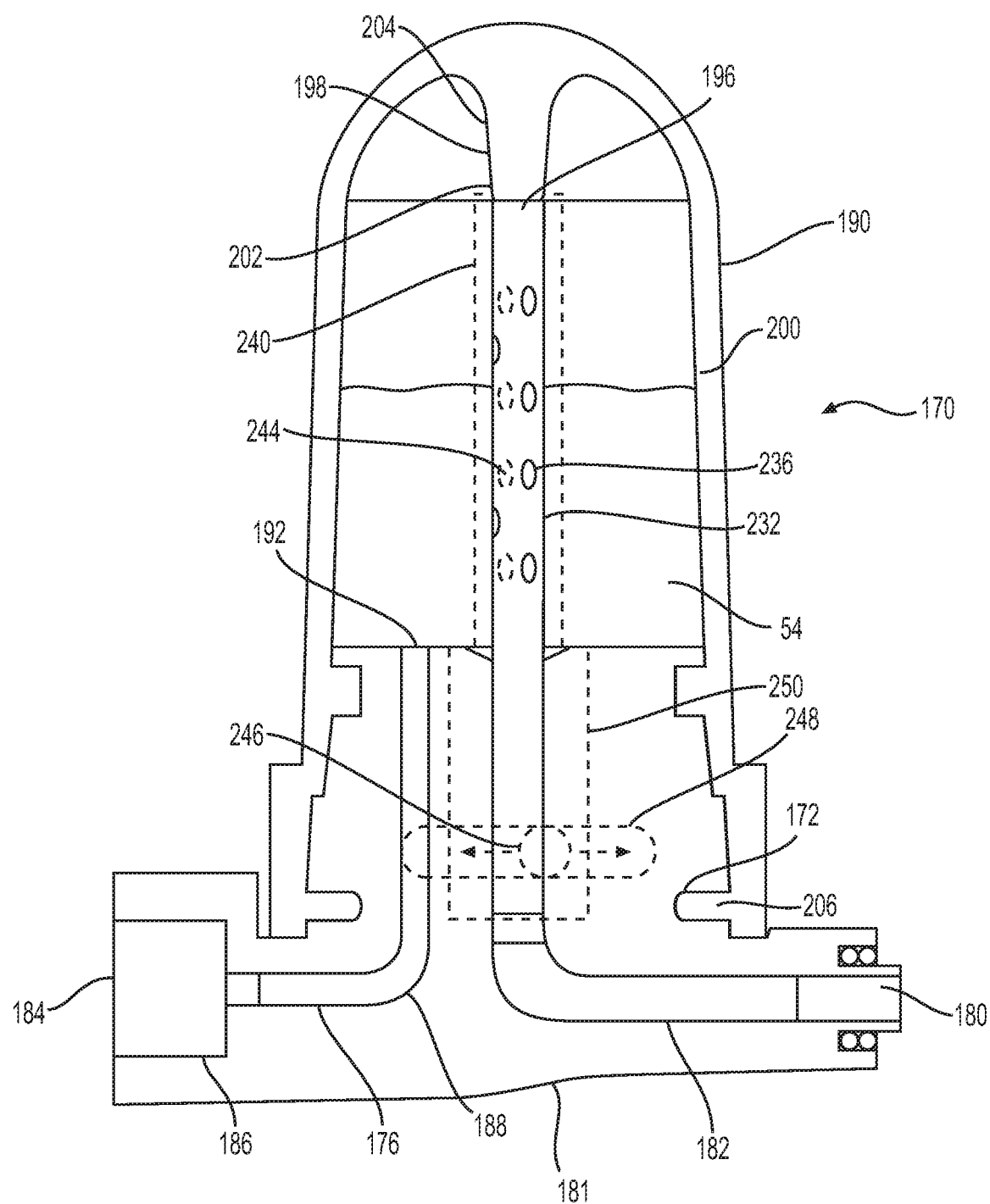
Figure 19B:
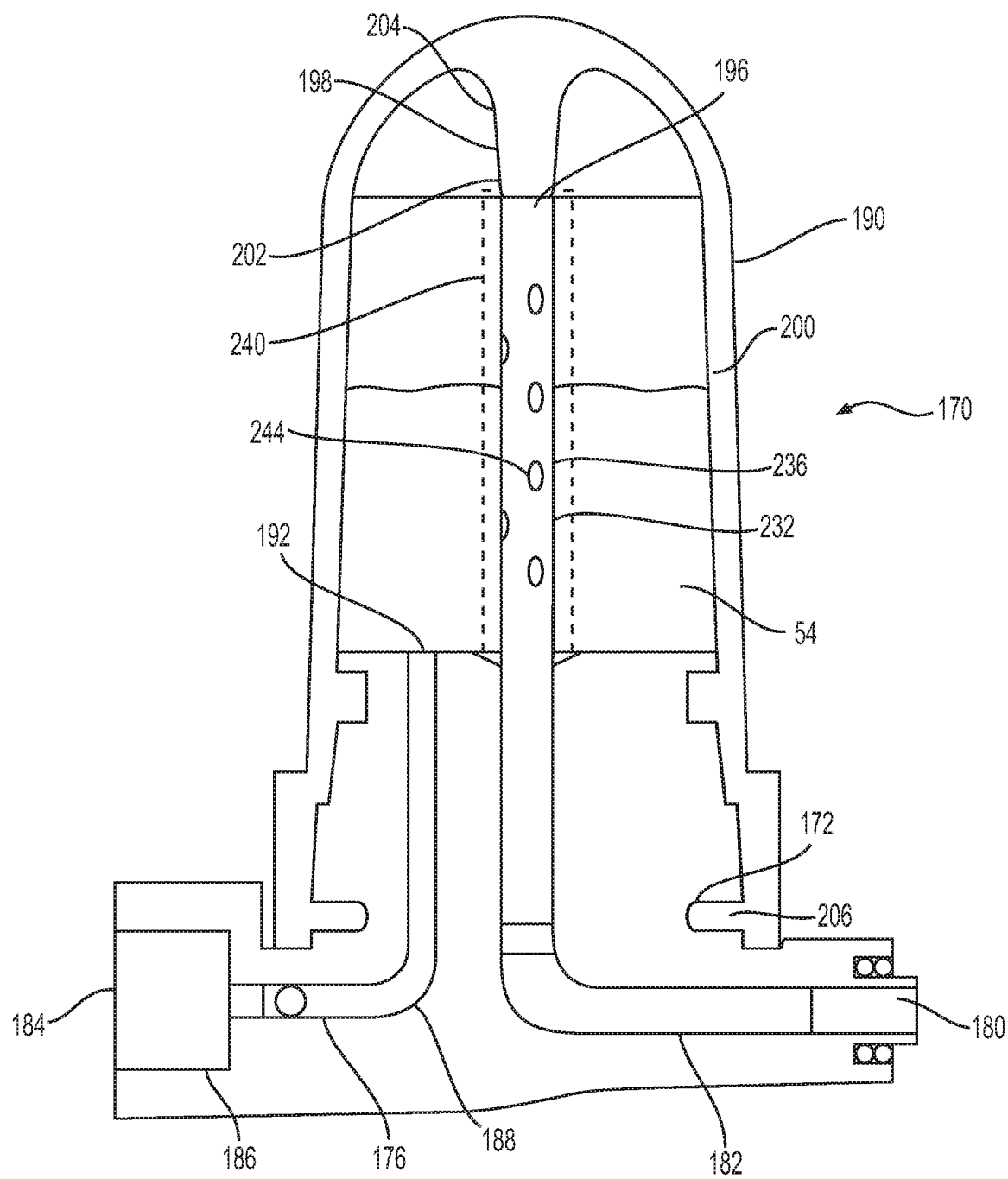

FIGS. 19A-B depict a portion of an assembly such as the assemblies described with regard to FIGS. 14-18. Any of the features described above or below may be used in conjunction with the features described herein with regard to FIGS. 19A-B. Turning to FIG. 19A, a passage 232 may be similar to passage 194, as described above with regard to FIGS. 14-16. Passage 232 may be a hypotube. Passage 232 may include perforations or voids 236 such as holes or slits. Perforations 236 may be of any suitable shape—for example, they may be circular, ovular, rectangular, square, or linear. Perforations 236 may also be of any suitable number and size. For example, perforations 236 may be large enough to allow passage of fluidized powdered agent 54 through the perforations 236.

An outer sleeve 240 may be disposed concentrically around and encompassing passage 232. For example, an inner surface of outer sleeve 240 may abut an outer surface of passage 232. Outer sleeve 240 may be made of the same or different material from passage 232. Outer sleeve 240 may be, for example, a hypotube. Outer sleeve 240 may have perforations or voids 244. Perforations 244 may have any of the qualities of perforations 236, described above. In the alternative, perforations 244 may have different qualities (such as shape or size) from perforations 236. Perforations 244 may be on locations of outer sleeve 240 which correspond to the locations of perforations 236 on passage 232. For example, perforations 244 may be located at the same height as perforations 236, and the spacing between perforations 244 may be proportional to the spacing between perforations 236. Perforations 244 may be the same size as perforations 232 or a different size from perforations 232. For example, perforations 244 may be larger than perforations 232.

One or both of passage 232 and outer sleeve 240 may be rotatable around a longitudinal axis of passage 232 and/or outer sleeve 240. For example, passage 232 and/or outer sleeve 240 may be rotatable by rotating powder chamber 190 to rotate one of passage 232 and outer sleeve 240 relative to the other, via engagement between protrusion 198 and passage 232 or outer sleeve 240; by sliding an actuator coupled to one of passage 232 and outer sleeve 240, to thereby rotate one of passage 232 and outer sleeve 240 relative to the other, with the actuator being accessible from an exterior of mixing chamber 181, or by any other suitable mechanism. The actuator may be coupled, for example, to an inner rotational member 246 of mixing chamber 181, which also may be coupled to one of passage 232 and outer sleeve 240, for rotating the one of passage 232 and outer sleeve 240 relative to the other. Alternatively, the actuator may be coupled, for example, to a lower end of passage 232, with passage 232 being slidably received by mixing chamber 181, for rotating passage 232 relative to sleeve 240. The actuator may include a knob or other protrusion 248 that may be accessible to a user. Protrusion 244 may, for example, extend through, and slide, within a slot 250 at a surface of mixing chamber 181.

Rotation of passage 232 and/or outer sleeve 240 may cause perforations 236 and 244 to become aligned or unaligned. For example, passage 232 may be fixed (non-rotatable), and outer sleeve 240 may be movable (rotatable). In a first (closed) configuration as shown in FIG. 19A, perforations 244 may not align with perforations 236. In the first (closed) configuration, powder chamber 190 may not be in fluid communication with passage 232 via perforations 244 and perforations 236. In the first (closed) configuration, fluidized powdered agent 54 may not be able to pass through perforations 244 and perforations 236 in order to enter passage 232.

In a second (open) configuration, as shown in FIG. 19B, outer sleeve 240 or passage 232 may be rotated with respect to the first configuration. In the second (open) configuration, perforations 244 may align with perforations 236 so that a powder chamber 190 is in fluid communication with passage 232 via perforations 244 and perforations 236. In the second (open) configuration, fluidized powdered agent 54 may be able to pass through perforations 244 and perforations 236 in order to enter passage 232

There may be numerous intermediate configurations of passage 232 and outer sleeve 240. For example, in certain configurations, perforations 244 and perforations 236 may partially align so that some fluidized powdered agent 54 may pass through perforations 244 and 236 to passage 232, but flow of fluidized powdered agent 54 is less than in an open configuration. Perforations 236 and 244 may be arranged to allow for a wide variety of configurations.

The features depicted in FIGS. 19A-B may be used alone or in combination with any of the configurations described with regard to FIGS. 14-18. For example, the features depicted in FIGS. 19A-B may be used in the alternative to moving powder chamber 190 up or down relative to mixing chamber 181. The features of FIGS. 19A-B may also be used in combination with movement of powder chamber 190 up or down relative to mixing chamber 181. For example, powder chamber 190 may be in a closed configuration (see FIG. 15), while passage 232 and outer sleeve 240 are in an open configuration. Thus, some amount of fluidized powdered agent 54 may be allowed to flow into passage 182 and out of opening 180. To allow additional fluidized powdered agent 54 to flow, powder chamber 190 may be transitioned into an open configuration (see FIG. 19B).

FIGS. 20-22 depict an assembly 270 of a powder chamber 272 and a mixing chamber 274. Assembly 270 may be used in conjunction with chassis 12 as depicted in FIG. 1, in place of powder chamber 16 and mixing chamber 38. In the alternative, assembly 270 may be used in place of any of the other powder and mixing chamber assemblies described herein.

Powder chamber 272 may include any suitable receptacle for holding powdered agent 54. Powder chamber 272 may include, for example, a substantially rigid vessel, such as a bottle. Powder chamber 272 may be fixedly attached or removably attached to any suitable chassis, such as chassis 12 or any other aforementioned chassis. In FIG. 20, powder chamber 272 is attached to mixing chamber 274. Reloading assembly 270 with powdered agent 54 may include removing a cap, cover, or the like from powder chamber 272, and pouring powdered agent 54 into powder chamber 272, or swapping out an empty assembly 270 for a full assembly 270. Where powder chamber 272 is removably attached to mixing chamber 274, reloading may include removing an empty powder chamber 272 from mixing chamber 274, and coupling a full powder chamber 272 to mixing chamber 274.

As shown in FIG. 20, mixing chamber 274 may include one or more helical grooves 276. Powder chamber 272 may include one or more radially-inwardly-extending protrusions or threads 278 (see FIG. 22) slidably received in the one or more helical grooves 276. As powder chamber 272 is rotated in a first direction (e.g., a clockwise direction), engagement between protrusions 278 and the one or more helical grooves 276 may move powder chamber 272 downward toward mixing chamber 274. As powder chamber 272 is rotated in a second direction (e.g., a counterclockwise direction) opposite the first direction, engagement between the protrusions 278 and the one or more helical grooves 276 may move powder chamber 272 upward away from mixing chamber 274. Powder chamber 272 may include a base or wider portion 280. Wider portion 280 may serve as a gripping portion for a user to rotate powder chamber 272.

Assembly 270 may include a passage 282 for directing pressurized gas. Flow of pressurized gas through passage 282 or any other passage described herein may be controlled by metering orifices located in any suitable position. Mixing chamber 274 may also include an opening 286 and a passage 288, wherein pressurized fluid from passage 282 may direct fluidized powdered agent 54 to opening 286 and out of mixing chamber 274, or may bypass powdered agent 54 so only pressurized fluid is emitted from opening 286.

Figure 21:
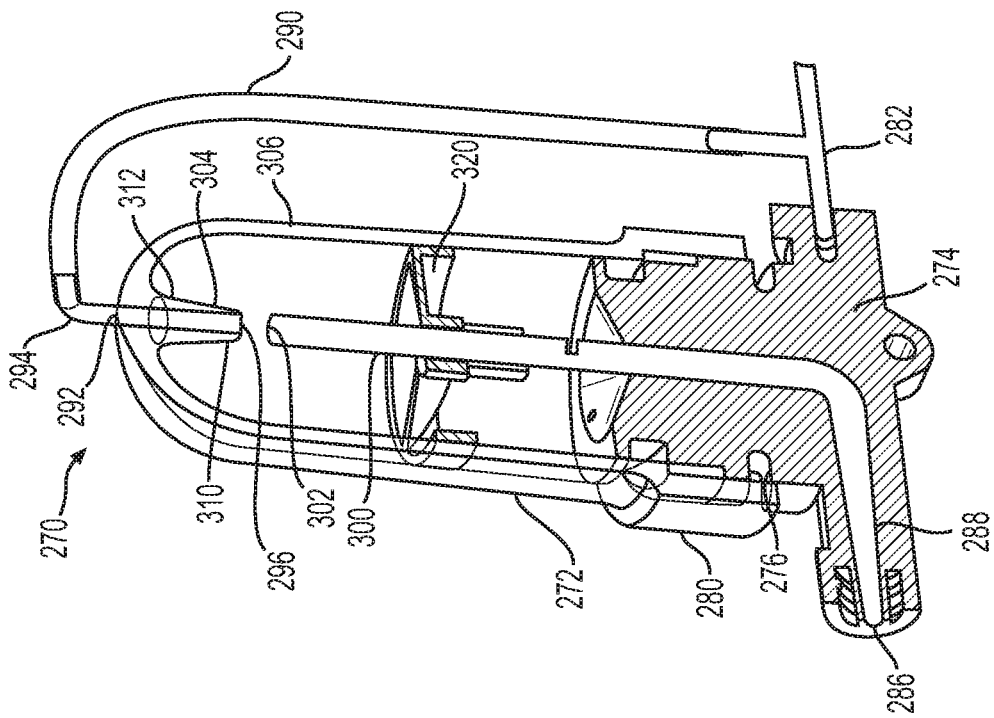
Figure 20:
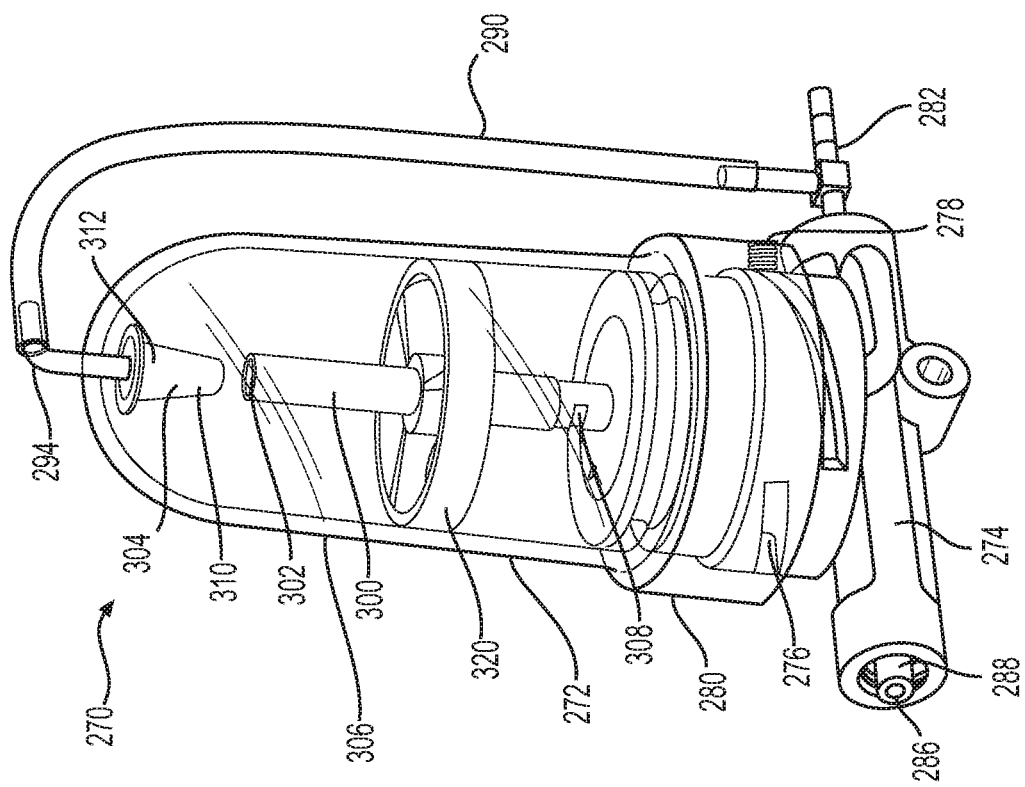

FIGS. 20-21 depict assembly 270 in an open position that may allow fluidized powdered agent 54 to flow. Assembly 270 may include a pressurized fluid flowpath, similar to the one described with regard to FIGS. 14-17, which includes opening 184, passage 176, and opening 192 for receiving pressurized fluid from passage 282 and directing the pressurized fluid into powder chamber 272. Passage 282 may connect to a bypass passage 290. Passage 290 may be integral with passage 282 or may be a separate component. If passage 290 is a separate component, passage 282 and passage 290 may be fixedly or removably attached to one another. For example, passage 282 and passage 290 may be separable from one another for the purposes of, for example, removing and replacing powder chamber 272 or otherwise refilling powder chamber 272. Passage 290 may be made of substantially rigid material, for example plastic or glass. Passage 290 may extend from passage 282 or another portion of mixing chamber 274 toward a top of powder chamber 272. Passage 290 may be separate from or integral with powder chamber 272 or another component of apparatus 270.

A portion of powder chamber 272 such as a top portion of powder chamber 272 may include an opening 292 (see FIG. 21). A passage 294 may pass through opening 292. Passage 294 may be fixedly or removably connected to passage 290. For example, passage 290 and passage 294 may be separable from one another for the purposes of, for example, removing and replacing powder chamber 272 or otherwise refilling powder chamber 272. In the alternative, passage 290 and passage 294 may be integral. Passage 294 may be made of any material that passage 290 may be made from or may be made from a different material. While passage 294 is shown passing through an opening 292 in a top surface of powder chamber 272, passage 290 and/or passage 294 may be configured so that they pass below powder chamber 272 and bypass powder chamber 272 in that manner.

When assembly 270 is in an open position as shown in FIGS. 20-21, pressurized gas may enter powder chamber 272 through an opening 296 and opening 192 (see FIG. 21). Opening 296 may be near the top of powder chamber 272 and may be at an end of passage 294. Powder chamber 272 may contain powdered agent 54. The pressurized gas exiting openings 192 and 296 may fluidize powdered agent 54 within powder chamber 272. While FIG. 20 depicts passage 294 extending vertically toward opening 296, it also is contemplated that passage 294 may extend at an angle toward opening 296, such that passage 294 may be tilted from the orientation shown in FIG. 20. Additionally or alternatively, passage 294 may extend along a helical path to opening 296. This may result in the pressurized gas being introduced into powder chamber 272 in the form of a swirling vortex, to fluidize powdered agent 54. In addition or in the alternative, the inside walls of passage 294 may include straight or curved grooves or protrusions to facilitate creation of a vortex by pressurized gas.

Assembly 270 may also include passage 300. Passage 300 may include a top opening 302. Passage 300 may be in fluid connection with passage 288. Passage 300 may have a longitudinal axis which is coaxial with, or parallel to, a longitudinal axis of powder chamber 272. Powder chamber 272 may also include a protrusion 304 extending downwardly from a top portion of an outer wall 306. Passage 294 may extend through protrusion 304. For example, passage 294 may be parallel to or coaxial with a longitudinal axis of protrusion 304. Protrusion 304 may have a lower portion 310 with a cross section narrower than opening 302. Protrusion 304 may taper so that an upper portion 312 of protrusion 304 has a cross section wider than opening 302. Protrusion 304 may be aligned with passage 300 so that lower portion 310 of protrusion 304 may enter passage 300 via opening 302, thereby plugging opening 302, either partially or fully depending on the depth of insertion of lower portion 310 into passage 300, to put assembly 270 in a closed position (see FIG. 22). In an open position, lower portion 310 of protrusion 304 may not be inside of passage 300, or protrusion 304 may otherwise not block opening 302. Passage 300 may be in fluid connection with both the interior of powder chamber 272 and passage 288 when assembly 270 (or powder chamber 272) is in the open position. When powder chamber 272 is the open position, fluidized powdered agent 54 may thus enter opening 302, pass through passage 300, and eventually pass through passage 288 and out opening 286. Powdered agent 54 also may enter a slot 308, pass through passage 300, and pass through passage 288 for emission from opening 286.

It also is contemplated that assembly 270 may have a plurality of open positions that allow different levels of flow of fluidized powdered agent 54 through passage 300. For example, the greater the distance between protrusion 304 and opening 302, the greater the flow of fluidized powdered agent 154 into opening 302. Decreasing the distance may reduce the flow, while still allowing flow at the reduced level.

One or more curved surfaces a top portion of powder chamber 272, in conjunction with the tapering surfaces of protrusion 304, may funnel or otherwise facilitate flow of fluidized powder agent 54 toward a central longitudinal axis of powder chamber 272, and toward opening 302 of passage 300. Side walls of powder chamber 272 may be tapered, such that powder chamber gets narrower as it extends upward, to help direct fluidized powder agent 54 into passage 300.

FIG. 22 depicts assembly 270 in a closed position that may prevent or limit the flow of fluidized powdered agent 54. To transition assembly 270 from the open position to the closed position, powder chamber 272 may be rotated relative to mixing chamber 274. Such rotation may cause movement of one or more protrusions or threads 276 in helical grooves 276. Powder chamber 272 may thus be moved downward. Protrusion 304 may move downward so that lower portion 310 is inside of passage 300, or so that protrusion 304 is otherwise blocking opening 302. Protrusion 304 may slide along passage 294, effectively closing the gap between passage 294 and passage 300.

Assembly 270 may also include a fluid randomizer 320 such as fluid randomizer 220 as described with regard to FIG. 18. A fluid randomizer 320 used in conjunction with assembly 270 may have any of the properties described above with regard to fluid randomizer 220. In one example, fluid randomizer 320 may be fixedly attached to an interior surface of powder chamber 272, such that fluid randomizer 320 may move as a unit with powder chamber 272. Fluid randomizer 320 may be slidably attached to passage 300, such that fluid randomizer 320 may rotate about, and slide longitudinally along, the exterior surface of passage 300. In the closed position of assembly 270, downward movement of powder chamber 272 may cause downward movement of fluid randomizer 320. When protrusion 304 blocks opening 302, a lower portion (e.g., a lower sleeve) of fluid randomizer 320 may block slot 308. Pressure may quickly build up in powder chamber 272 due to its exit openings (opening 302 and slot 308) being covered. As such, pressurized fluid in passage 282 may not flow into passage 176, but rather, may seek the path of least resistance through bypass passage 290, into passage 300 (thereby bypassing the interior of powder chamber 272), and out through passage 288. Powdered agent 54 will not flow in such a configuration. A closed position allowing the passage of pressurized gas but not of powdered agent may be desirable, for example, for administering pressurized gas inside a body of a patient, prevent bodily fluids from entering apparatus 270 through its distal end/tip, and/or flushing out apparatus 270.

In one example, bypass passage 290 may be configured so that it is sufficiently narrow or otherwise occlusive so that pressurized air will not flow through bypass passage 290 so long as slot 308 is not blocked. Because pressurized gas may more easily flow through opening than bypass passage 290, no or essentially no gas or only a small amount of gas may flow through bypass passage 290 so long as pressurized gas and/or fluidized powdered agent 54 are able to exit the powder chamber 272 via slot 308 and/or opening 302. If slot 308 and opening 302 are both blocked, then pressurized gas may seek the path of least resistance and pass through bypass passage 290. In other words, pressurized gas may only flow through bypass passage 290 at all or in an appreciable amount if slot 308 and opening 302 are blocked, rendering bypass passage 290 the path of least resistance. Powdered agent 54 will not flow in such a configuration. A closed position allowing the passage of pressurized gas but not of powdered agent may be desirable, for example, for administering pressurized gas inside a body of a patient, prevent bodily fluids from entering apparatus 270 through its distal end/tip, and/or flushing out apparatus 270.

Figure 17:
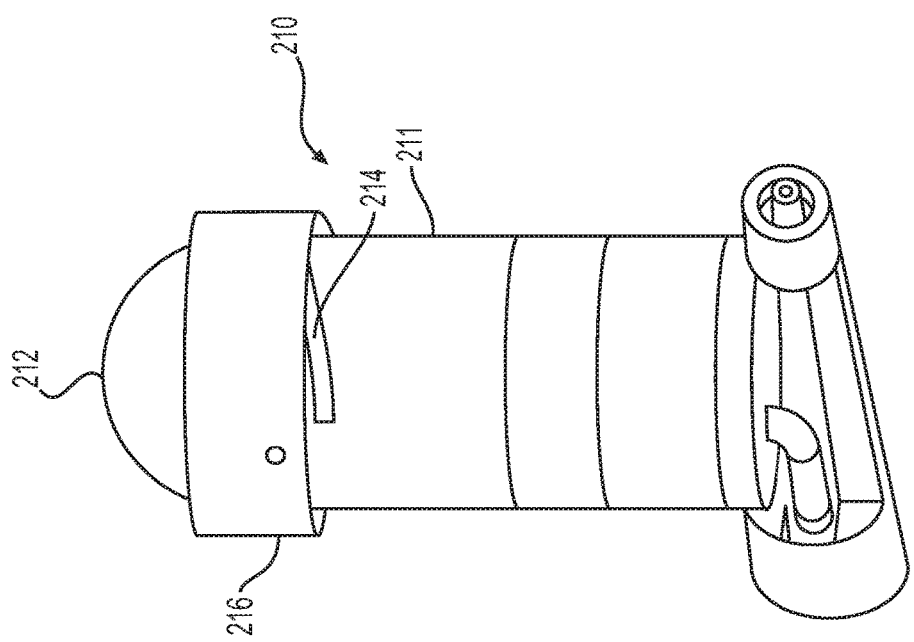

Similar to the configuration shown in FIG. 17 above with respect to apparatus 170, an apparatus such as apparatus 270 may include a powder chamber with a removable cap. In such a configuration, an upper portion of the powder chamber may have one or more helical grooves on its exterior. The cap may have a wider bottom portion configured to receive the upper portion of the powder chamber. The cap may be rotated relative to the upper portion of the powder chamber to transition the assembly from an open position similar to that shown in FIG. 21, to a closed position similar to that shown in FIG. 22. The bottom portion or another portion of the cap may include one or more protrusions or threads, similar to one or more protrusions/threads 278 (FIG. 20), which fit in a helical groove and facilitate moving the cap from a lower, closed position to a raised, open position.

Figure 22:
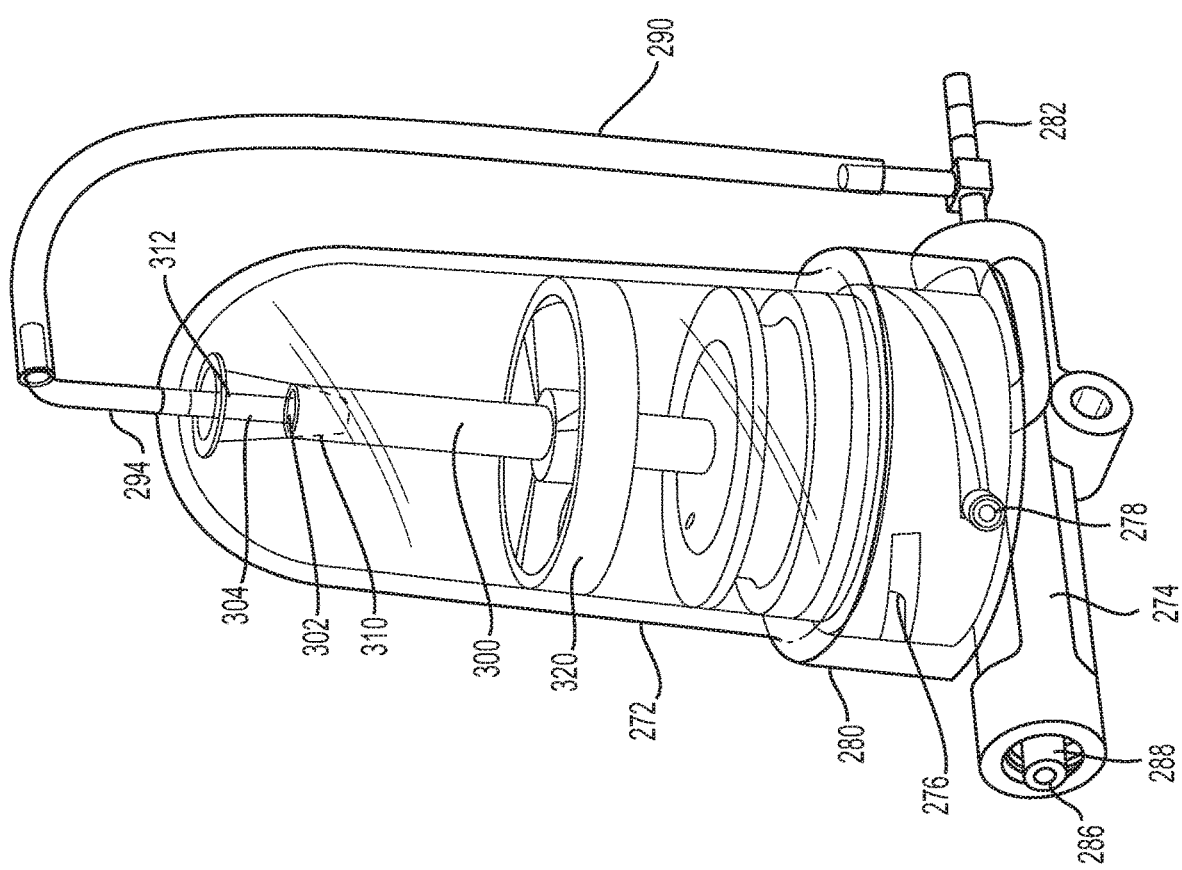

The operation may be similar to that as explained above for assembly 270 as described with regard to FIGS. 20-22 in other respects.

Assembly 270 may alternatively or additionally make use of any of the features described with regard to FIGS. 19A-B. For example, rather than raising powder chamber 272 to allow for flow powdered agent 54 through passage 288 and out of opening 286, rotation of a passage such as passage 232 or an outer sleeve such as outer sleeve 240 may enable flow of powdered agent 54 through passage 288 and out of opening 286. In the alternative, as described above with regard to FIGS. 19A-B, the rotation of a passage such as passage 232 or an outer sleeve such as outer sleeve 240 may permit for some flow of fluidized powdered agent through passage 288 and out of opening 286. Transitioning powder chamber 272 into an open position (see FIGS. 20-21) may allow further flow of fluidized powdered agent 54 through passage 288 and out of opening 286.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. An apparatus for delivering a powdered agent into a subject's body, the apparatus comprising:
    a first passage for receiving a pressurized gas;
    a container housing a powdered agent, wherein the container is in fluid connection with the first passage, and wherein at least a portion of the pressurized gas is introduced into the powdered agent in the container to mix the powdered agent; and
    a second passage including an opening for receiving the powdered agent from the container, the second passage is configured to move between a closed position and an open position when the container is coupled to the apparatus;
    wherein in a first configuration of the apparatus with the container coupled to the apparatus, the second passage is in the closed position and the opening is in a closed state, to restrict the powdered agent from exiting the container and entering the second passage, such that the second passage is not in fluid connection with the container;
    wherein in a second configuration of the apparatus with the container coupled to the apparatus, the second passage is in the open position and the opening is in an open state, to allow the powdered agent to exit the container and enter the second passage, such that the second passage is in fluid connection with the container; and
    wherein, while the container remains coupled to the apparatus, the apparatus is configured to transition between the first configuration and the second configuration by relative rotation between the container and the second passage, thereby moving the second passage between the closed position and the open position.

2. The apparatus of claim 1, wherein the container has a longitudinal axis, wherein the second passage has a longitudinal axis, and wherein the longitudinal axis of the second passage is parallel to or coaxial with the longitudinal axis of the container.

3. The apparatus of claim 2, wherein the longitudinal axes of the container and the second passage are coaxial.

4. The apparatus of claim 1, wherein the second passage extends into the container.

5. The apparatus of claim 1, further comprising:
at least one helical groove; and
at least one protrusion movably disposed within the at least one helical groove,
wherein the at least one protrusion moves in the at least one helical groove during a transition between the first configuration and the second configuration.

6. The apparatus of claim 1, wherein the apparatus further comprises a protrusion, wherein the protrusion is configured to prevent the passage of the powdered agent from the container to the second passage when the apparatus is in the first configuration.

7. The apparatus of claim 6, wherein at least a portion of the protrusion is inside the opening when the apparatus is in the first configuration.

8. The apparatus of claim 6, wherein the protrusion extends from a top wall of the container.

9. The apparatus of claim 1, wherein the container comprises a movable cap, and wherein the apparatus transitions from the first configuration to the second configuration upon twisting of the cap.

10. The apparatus of claim 1, wherein at least one interior wall of the container includes a curved surface that is configured to funnel the powdered agent towards a central longitudinal axis of the container to facilitate flow of the powdered agent and the pressurized gas into the opening of the second passage.

11. An apparatus for delivering a powdered agent, comprising:
a first passage in fluid communication with a pressurized gas;
a second passage having an inlet opening and an outlet opening, the outlet opening is in fluid communication with a catheter of the apparatus, the second passage is configured to move between a closed position and an open position; and
a container housing the powdered agent, wherein the second passage is configured to selectively couple the catheter to the container in response to transitioning between the closed position and the open position by relative rotation between the container and the second passage while the container is coupled to the apparatus;
wherein, when in the closed position of the second passage and with the container coupled to the apparatus, each of the inlet opening and the outlet opening is not in fluid communication with the container such that the powdered agent is inhibited from moving through the second passage and to the catheter; and
wherein, when in the open position of the second passage and with the container coupled to the apparatus, each of the inlet opening and the outlet opening is in fluid communication with the container such that the powdered agent is permitted to move through the second passage and to the catheter.

12. The apparatus of claim 11, wherein at least a portion of the pressurized gas is introduced into the container via the first passage to mix with the powdered agent within the container.

13. The apparatus of claim 12, wherein the second passage is configured to deliver the powdered agent and the pressurized gas to the catheter when the second passage is in the open position.

14. The apparatus of claim 11, wherein, when the second passage is in the open position, a longitudinal axis of the second passage is coaxial with a longitudinal axis of the container.

15. The apparatus of claim 11, wherein at least a portion of the apparatus is configured to move relative to the container to transition the second passage from the closed position to the open position.

16. The apparatus of claim 15, wherein the portion of the apparatus includes an impediment that is configured to close the inlet opening of the second passage when in the closed position.

17. The apparatus of claim 16, wherein the impediment is configured to move and open the inlet opening when the second passage is in the open position to fluidly couple the container to the second passage.

18. The apparatus of claim 15, wherein the second passage is transitioned from the closed position to the open position in response to the portion of the apparatus rotating relative to the container.

19. The apparatus of claim 11, wherein the first passage is in fluid communication with the second passage at least when the second passage is in the open position.

20. An apparatus for delivering a powdered agent, comprising:
a first passage fluidly coupled to a fluid source;
a second passage fluidly coupled to a catheter of the apparatus; and
a container housing the powdered agent, the container is selectively fluidly coupled to the catheter via the second passage, in response to relative rotation between the container and the second passage as the container is coupled to the apparatus;
wherein the second passage is configured to fluidly decouple the container from the catheter when the container is coupled to the apparatus and an opening of the second passage is closed, thereby inhibiting the catheter from receiving the powdered agent from the container and fluid from the fluid source; and
wherein the second passage is configured to fluidly couple the container to the catheter when the container remains coupled to the apparatus and the opening of the second passage is open, upon relative rotation between the container and the second passage, thereby permitting the catheter to receive the powdered agent from the container and the fluid from the fluid source through the second passage.

* * * * *